United States Patent
Dickerson et al.

(10) Patent No.: US 10,507,033 B2
(45) Date of Patent: Dec. 17, 2019

(54) ULTRASONIC SURGICAL INSTRUMENT WITH REPLACEABLE CLAMP PAD

(71) Applicant: Ethicon Endo-Surgery, LLC, Guaynabo, PR (US)

(72) Inventors: Benjamin D. Dickerson, Cincinnati, OH (US); Steven P. Smolik, West Chester, OH (US); David J. Cagle, Cincinnati, OH (US); Jeffrey D. Messerly, Cincinnati, OH (US); Frederick L. Estera, Cincinnati, OH (US); Paul F. Riestenberg, North Bend, OH (US); Charles J. Scheib, Loveland, OH (US); Tylor C. Muhlenkamp, Cincinnati, OH (US); Kristen G. Denzinger, Cincinnati, OH (US); Ryan M. Asher, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 928 days.

(21) Appl. No.: 14/836,347

(22) Filed: Aug. 26, 2015

(65) Prior Publication Data
US 2017/0056059 A1  Mar. 2, 2017

(51) Int. Cl.
*A61B 17/32* (2006.01)
*A61B 17/28* (2006.01)
*A61B 17/00* (2006.01)

(52) U.S. Cl.
CPC ............ *A61B 17/320092* (2013.01); *A61B 2017/00017* (2013.01); *A61B 2017/00424* (2013.01);
(Continued)

(58) Field of Classification Search
CPC .... A61B 2017/2829; A61B 2017/2825; A61B 2017/320072; A61B 17/320068;
(Continued)

(56) References Cited

U.S. PATENT DOCUMENTS

| | | | |
|---|---|---|---|
| 4,452,244 A | 6/1984 | Chin | |
| 5,250,072 A * | 10/1993 | Jain | A61B 17/282 606/205 |

(Continued)

FOREIGN PATENT DOCUMENTS

| | | |
|---|---|---|
| EP | 0490301 A1 | 6/1992 |
| WO | WO 93/21836 A1 | 11/1993 |

(Continued)

OTHER PUBLICATIONS

International Search Report and Written Opinion dated Oct. 20, 2016 for Application No. PCT/US2016/047341, 13 pgs.
U.S. Appl. No. 61/410,603, filed Nov. 5, 2010.

*Primary Examiner* — Diane D Yabut
*Assistant Examiner* — Majid Jamialahmadi
(74) *Attorney, Agent, or Firm* — Frost Brown Todd LLC

(57) ABSTRACT

An ultrasonic instrument includes a body, a shaft assembly, and an end effector. The shaft assembly extends distally from the body. The shaft assembly includes an acoustic waveguide configured to acoustically couple with an ultrasonic transducer. The end effector includes an ultrasonic blade, a clamp arm and a clamp pad. The ultrasonic blade is in acoustic communication with the waveguide. The clamp arm is pivotally coupled with the shaft assembly. The clamp pad is configured to removably couple with the clamp arm while the clamp arm is pivotally coupled to the shaft assembly.

6 Claims, 27 Drawing Sheets

(52) U.S. Cl.
CPC ........... *A61B 2017/00473* (2013.01); *A61B 2017/2825* (2013.01); *A61B 2017/2829* (2013.01); *A61B 2017/320072* (2013.01); *A61B 2017/320074* (2017.08); *A61B 2017/320093* (2017.08); *A61B 2017/320094* (2017.08); *A61B 2017/320095* (2017.08)

(58) Field of Classification Search
CPC .......... A61B 17/320092; A61B 17/282; A61B 17/29; A61B 17/295; A61B 17/064; A61B 17/068; A61B 2017/2926
See application file for complete search history.

(56) References Cited

U.S. PATENT DOCUMENTS

| | | | |
|---|---|---|---|
| 5,322,055 A | 6/1994 | Davison et al. | |
| 5,324,299 A | 6/1994 | Davison et al. | |
| 5,873,873 A | 2/1999 | Smith et al. | |
| 5,980,510 A | 11/1999 | Tsonton et al. | |
| 6,024,750 A | 2/2000 | Mastri et al. | |
| 6,206,896 B1 | 3/2001 | Howell et al. | |
| 6,214,023 B1 | 4/2001 | Whipple et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,423,082 B1 | 7/2002 | Houser et al. | |
| 6,432,118 B1* | 8/2002 | Messerly ....... A61B 17/320092 606/169 | |
| 6,773,444 B2 | 8/2004 | Messerly | |
| 6,783,524 B2 | 8/2004 | Anderson et al. | |
| 7,544,200 B2 | 6/2009 | Houser | |
| 8,057,498 B2 | 11/2011 | Robertson | |
| 8,461,744 B2 | 6/2013 | Wiener et al. | |
| 8,591,536 B2 | 11/2013 | Robertson | |
| 8,623,027 B2 | 1/2014 | Price et al. | |
| 8,911,460 B2 | 12/2014 | Neurohr et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,381,058 B2 | 7/2016 | Houser et al. | |
| 9,393,037 B2 | 7/2016 | Olson et al. | |
| 2006/0079874 A1 | 4/2006 | Faller et al. | |
| 2007/0179526 A1* | 8/2007 | Hart ................ A61B 17/122 606/207 | |
| 2007/0191713 A1 | 8/2007 | Eichmann et al. | |
| 2007/0282332 A1* | 12/2007 | Witt ............ A61B 17/320092 606/50 | |
| 2007/0282333 A1 | 12/2007 | Fortson et al. | |
| 2008/0200940 A1 | 8/2008 | Eichmann et al. | |
| 2012/0116265 A1 | 5/2012 | Houser et al. | |
| 2013/0046337 A1* | 2/2013 | Evans ................ A61B 17/29 606/205 | |
| 2015/0080924 A1 | 3/2015 | Stulen et al. | |
| 2015/0148834 A1 | 5/2015 | Gee et al. | |
| 2015/0164532 A1 | 6/2015 | Faller et al. | |
| 2015/0245850 A1 | 9/2015 | Hibner et al. | |
| 2016/0143659 A1 | 5/2016 | Glutz et al. | |

FOREIGN PATENT DOCUMENTS

| | | |
|---|---|---|
| WO | WO 97/38632 A1 | 10/1997 |
| WO | WO 2007/047380 A2 | 4/2007 |

* cited by examiner

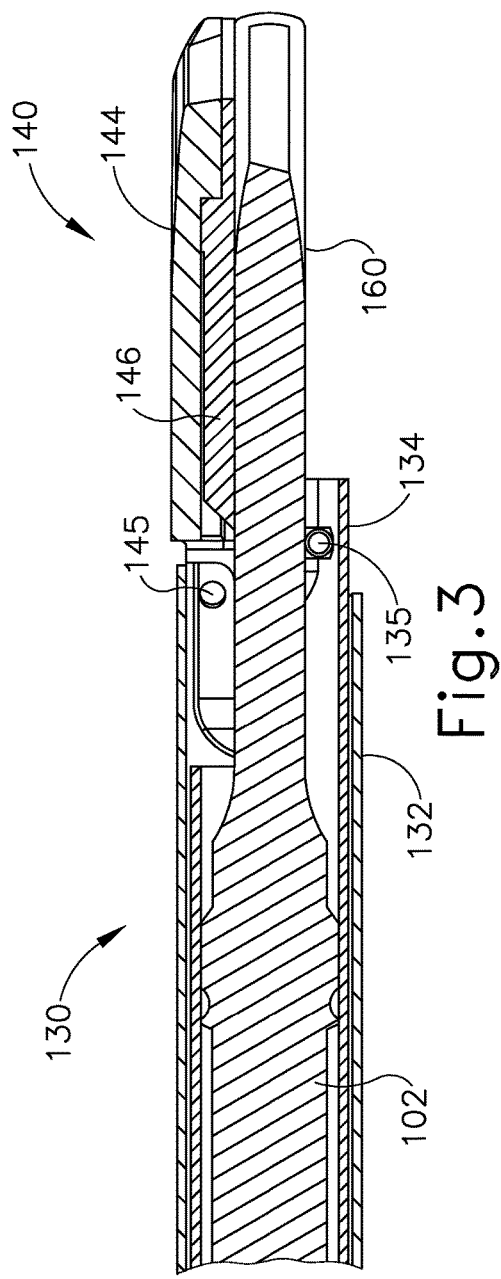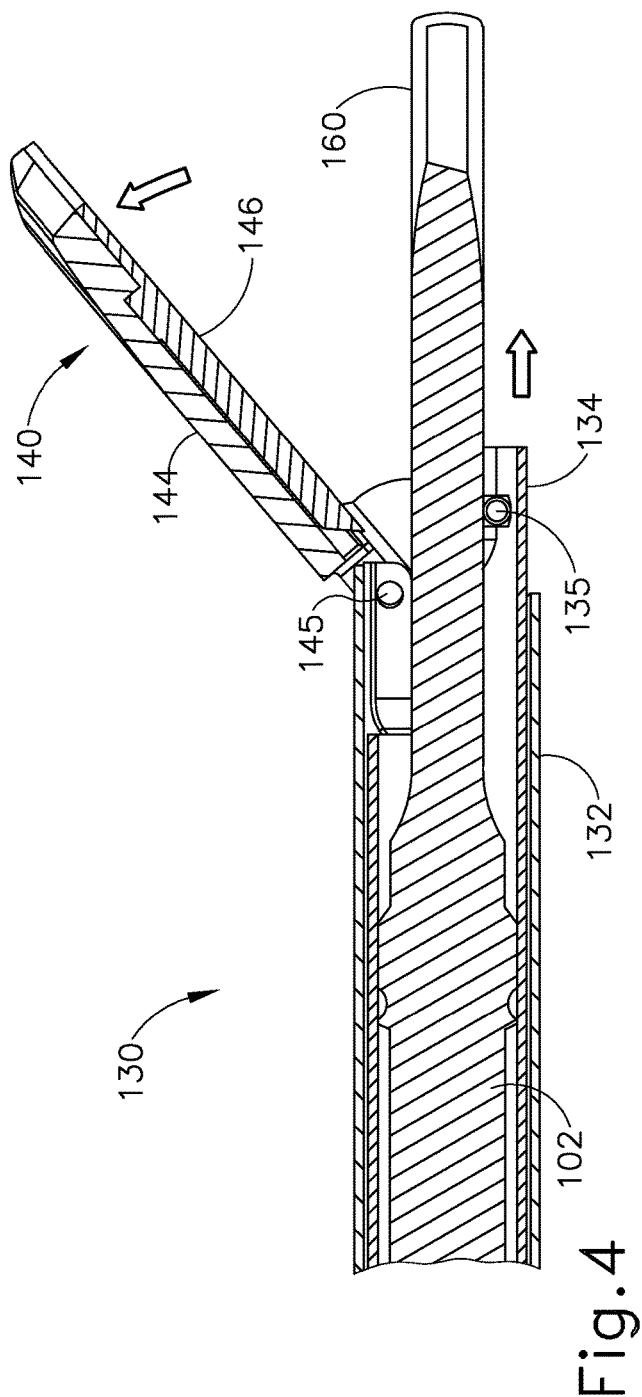

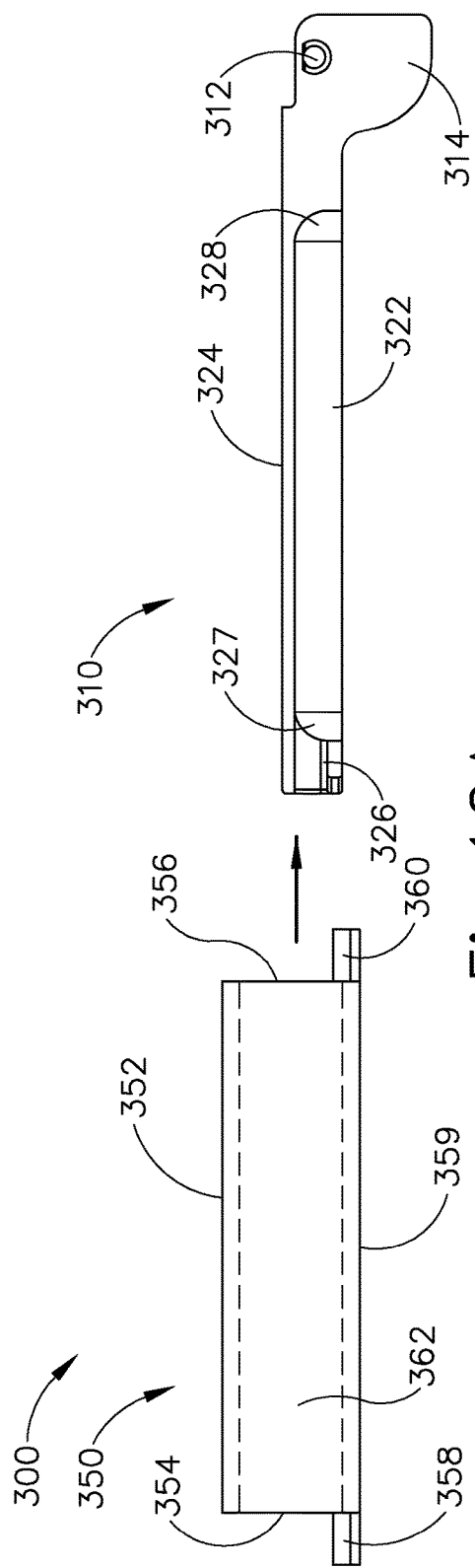
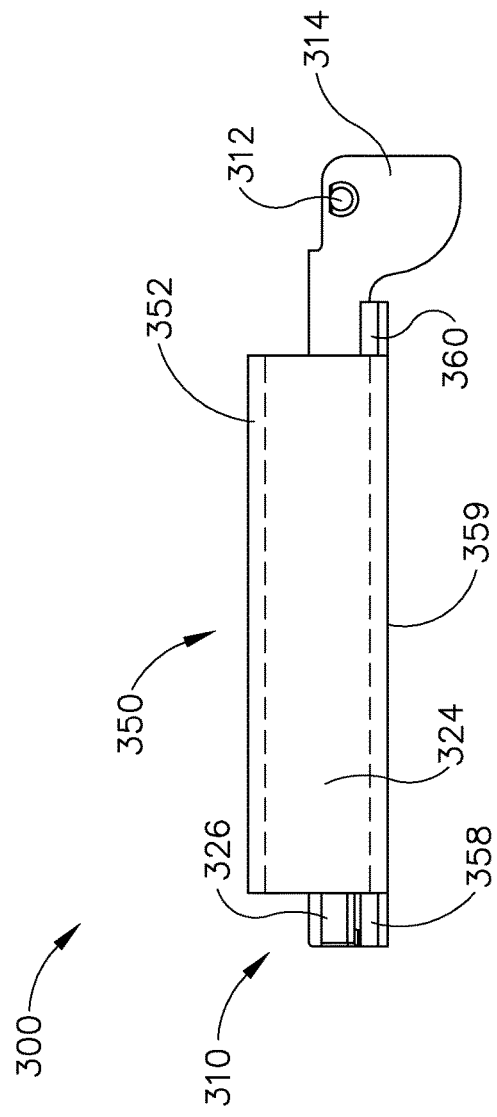

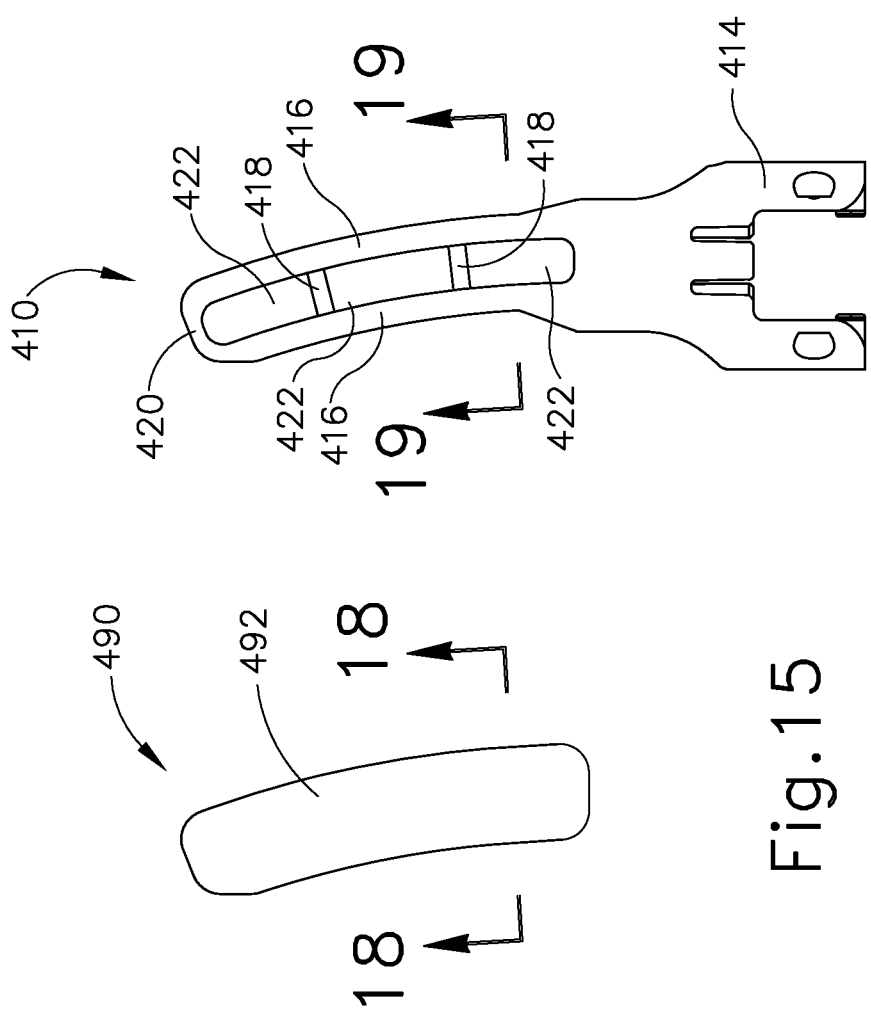

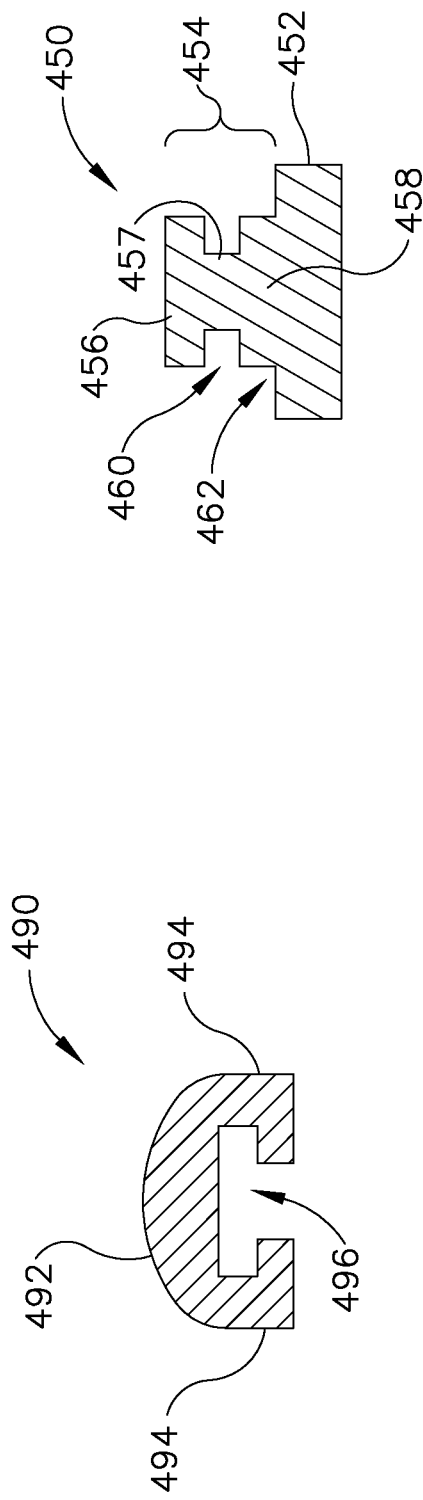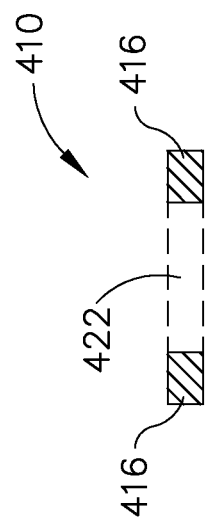
Fig.20
Fig.19
Fig.18

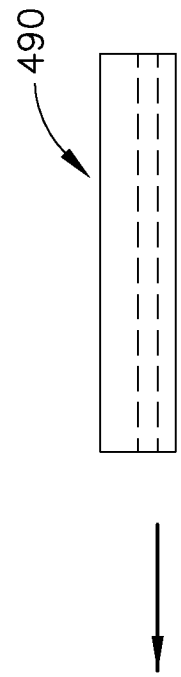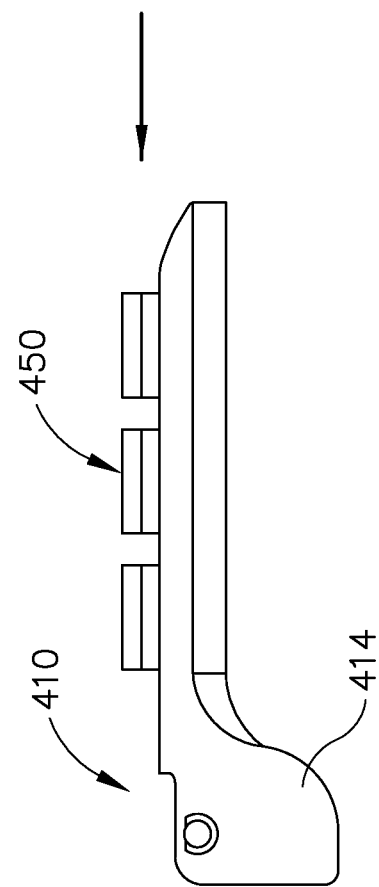

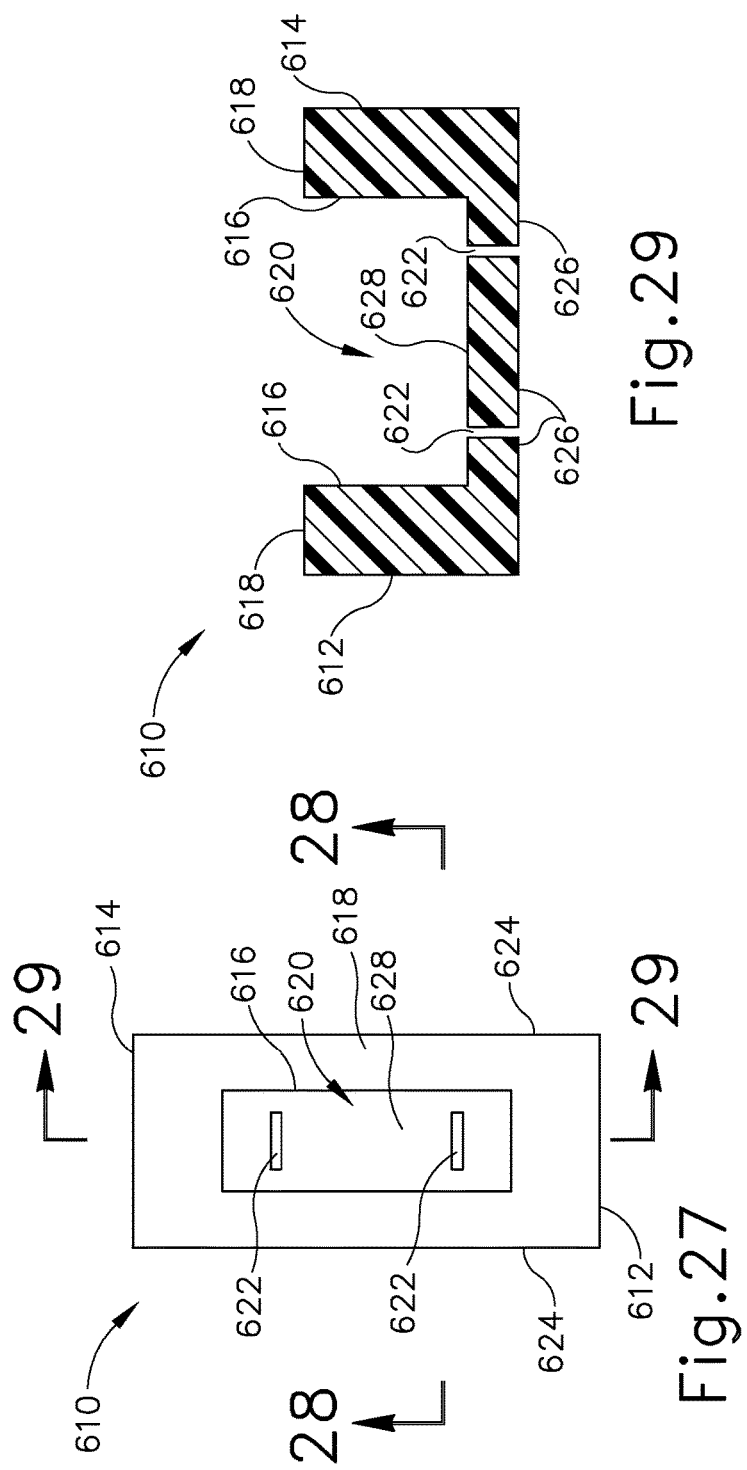

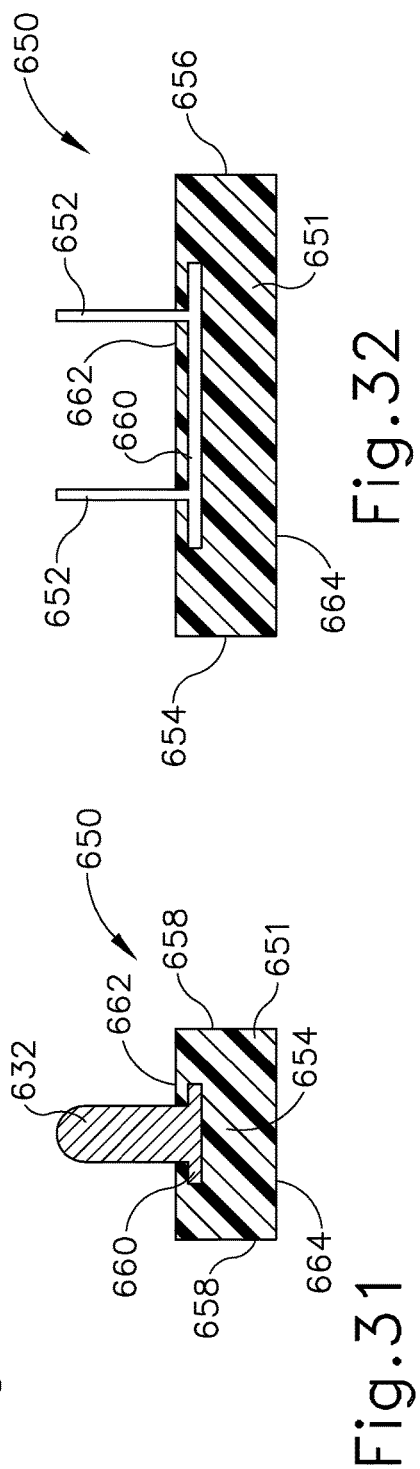
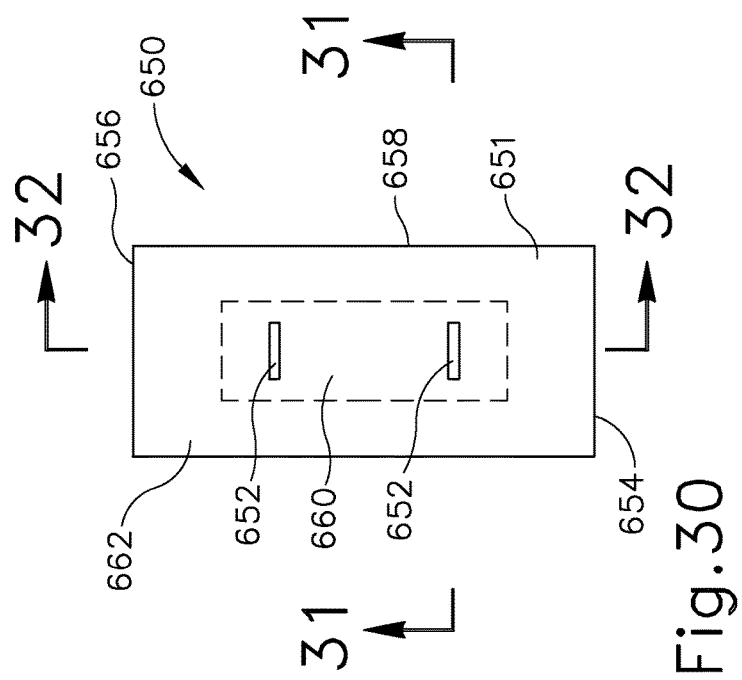

ULTRASONIC SURGICAL INSTRUMENT WITH REPLACEABLE CLAMP PAD

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. Some instruments have a clamp arm and clamp pad for grasping tissue with the blade element.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Clamp pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,026,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,383,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3 depicts a cross-sectional side view of an end effector of the instrument of FIG. 2 in a closed position;

FIG. 4 depicts a cross-sectional side view of the end effector of FIG. 3 in an open position;

FIG. 12A depicts a side elevational view of the clamp arm assembly of FIG. 11, with the clamp pad separated from the clamp arm;

FIG. 12B depicts a side elevational view of the clamp arm assembly of FIG. 11, with the clamp pad secured to the clamp arm;

FIG. 15 depicts a top plan view of an exemplary sliding lock that may be used as part of another exemplary alternative clamp arm assembly that may be incorporated into the end effector of FIG. 3;

FIG. 16 depicts a top plan view of an exemplary clamp arm that may be used with the sliding lock of FIG. 15 to form an exemplary alternative clamp arm assembly that may be incorporated into the end effector of FIG. 3;

FIG. 17 depicts a top plan view of an exemplary clamp pad that may be used with the sliding lock of FIG. 15 and the clamp arm of FIG. 16 to form an exemplary alternative clamp arm assembly that may be incorporated into the end effector of FIG. 3;

FIG. 18 depicts a cross-sectional view of the sliding lock of FIG. 15, taken along line 18-18 of FIG. 15;

FIG. 19 depicts a cross-sectional view of the clamp arm of FIG. 16, taken along line 19-19 of FIG. 16;

FIG. 20 depicts a cross-sectional view of the clamp pad of FIG. 17, taken along line 20-20 of FIG. 17;

FIG. 22A depicts a cross-sectional view of the clamp pad of FIG. 17 placed under the clamp arm of FIG. 16;

FIG. 22B depicts a cross-sectional view of a portion of the clamp pad of FIG. 17 positioned in the clamp arm of FIG. 16;

FIG. 22C depicts a side view of the sliding lock of FIG. 15 being slid on the top of the clamp pad of FIG. 17 as the portion of the clamp pad of FIG. 17 is positioned in the clamp arm of FIG. 16;

FIG. 27 depicts a top view of a portion of the clamp arm of the clamp arm assembly FIG. 26A;

FIG. 28 depicts a cross-sectional view of the clamp arm of FIG. 27, taken along line 28-28 of FIG. 27;

FIG. 29 depicts a cross-sectional view of the clamp arm of FIG. 27, taken along line 29-29 of FIG. 27;

FIG. 30 depicts a top view of a portion of the clamp pad of the clamp arm assembly FIG. 26A;

FIG. 31 depicts a cross-sectional view of the clamp pad of FIG. 30, taken along line 31-31 of FIG. 30;

FIG. 32 depicts a cross-sectional view of the clamp pad of FIG. 30, taken along line 32-32 of FIG. 30;

Figure 1:
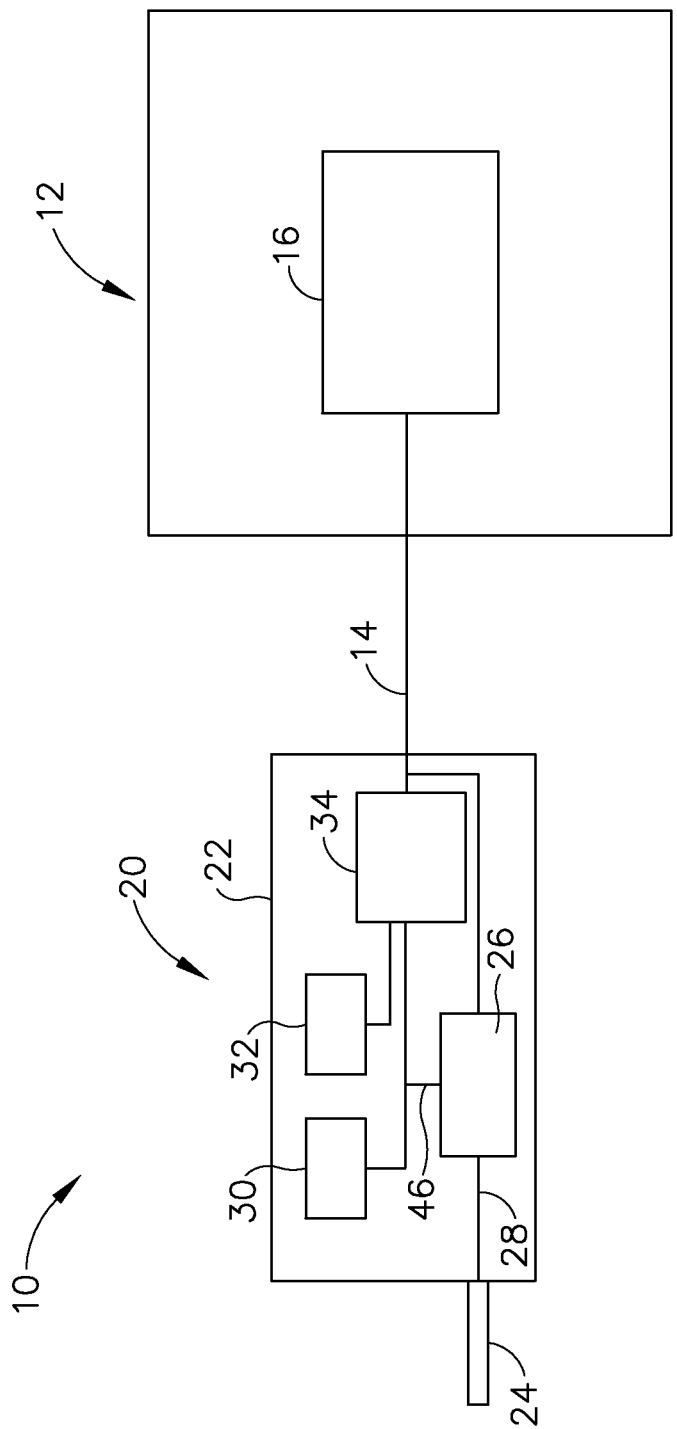
FIG. 1 depicts a block schematic view of an exemplary surgical system.
Figure 2:
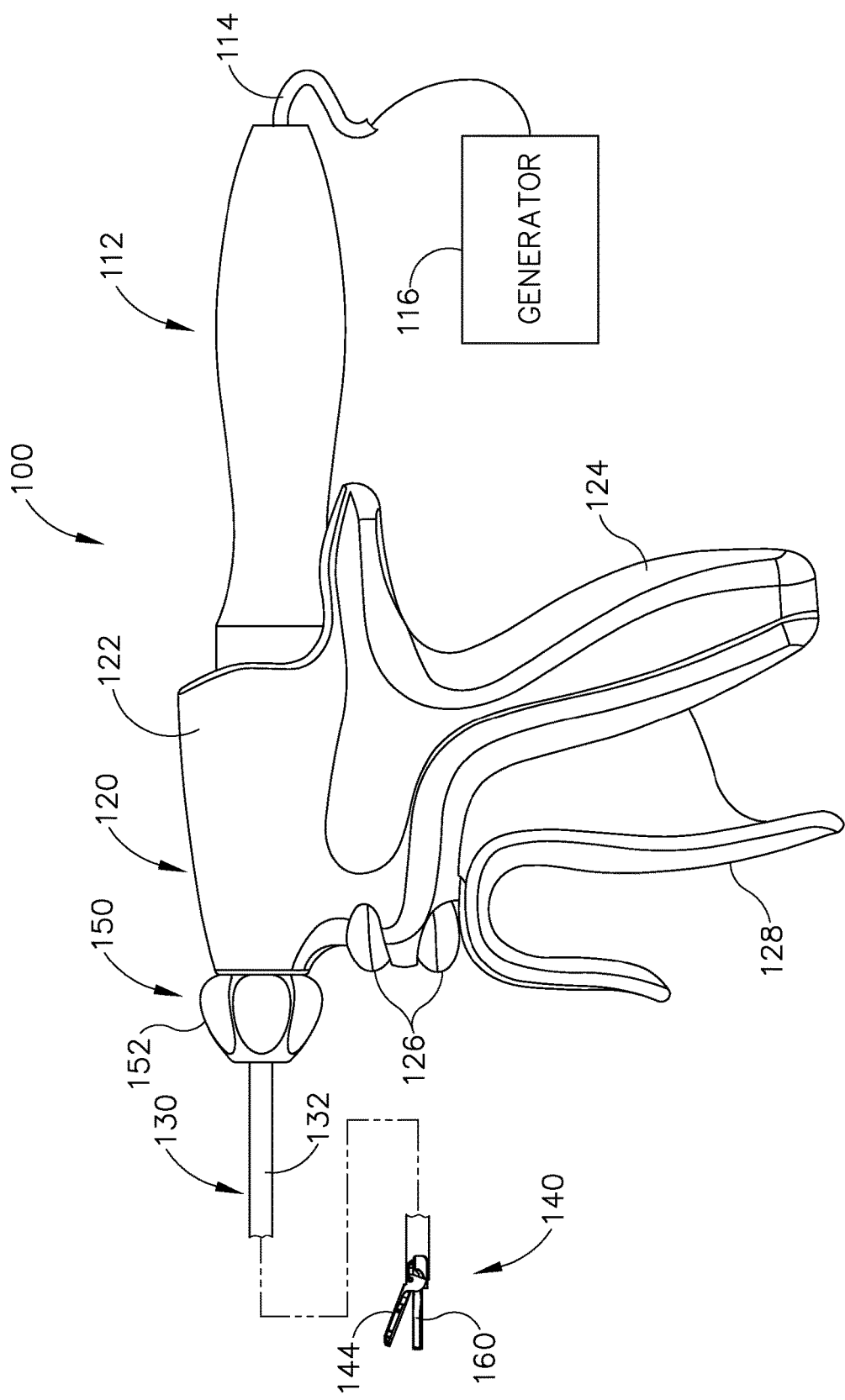
FIG. 2 depicts a side elevational view of an exemplary surgical instrument that may be incorporated into the system of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handle assembly (22), which is configured to be grasped in one hand (or two hands) of an operator and manipulated by one hand (or two hands) of the operator during a surgical procedure. For instance, in some versions, handle assembly (22) may be grasped like a pencil by the operator. In some other versions, handle assembly (22) may include a scissor grip that may be grasped like scissors by the operator. In some other versions, handle assembly (22) may include a pistol grip that may be grasped like a pistol by the operator. Of course, handle assembly (22) may be configured to be gripped in any other suitable fashion. Furthermore, some versions of instrument (20) may substitute handle assembly (22) with a body that is coupled to a robotic surgical system that is configured to operate instrument (20) (e.g., via remote control, etc.). In the present example, a blade (24) extends distally from the handle assembly (22). Handle assembly (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handle assembly (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (nλ/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handle assembly (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handle assembly (22). For instance, in some such versions, generator (12) only communicates one type of electrical power (e.g., just one voltage and/or current available) to handle assembly (22), and control circuitry (16) within handle assembly (22) is operable to modify the electrical power (e.g., the voltage of the electrical power), in accordance with selections made by the operator via control selector (30), before the electrical power reaches ultrasonic transducer (26). Furthermore, generator (12) may be incorporated into handle assembly (22) along with all other components of surgical system (10). For instance, one or more batteries (not shown) or other portable sources of power may be provided in handle assembly (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations of instrument (20). It should be understood that the various examples of instrument (20) described below may be readily incorporated into surgical system (10) as described above. It should also be understood that the various components and operabilities of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

FIGS. 2-5 illustrate an exemplary ultrasonic surgical instrument (100). At least part of instrument (100) may be constructed and operable in accordance with at least some of the teachings of U.S. Pat. Nos. 5,322,055; 5,873,873; 5,980, 510; 6,325,811; 6,773,444; 6,783,524; 8,461,744; 8,623, 027; U.S. Pub. No. 2006/0079874, now abandoned; U.S. Pub. No. 2007/0191713, now abandoned; U.S. Pub. No. 2007/0282333, now abandoned; U.S. Pub. No. 2008/ 0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028, 717, issued as U.S. Pat. No. 10,172,636 on Jan. 8, 2019. The disclosures of each of the foregoing patents, publications, and applications are incorporated by reference herein. As described therein and as will be described in greater detail below, instrument (100) is operable to cut tissue and seal or weld tissue (e.g., a blood vessel, etc.) substantially simultaneously. It should also be understood that instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (100) of the present example comprises a handle assembly (120), a shaft assembly (130), and an end effector (140). Handle assembly (120) comprises a body (122) including a pistol grip (124) and a pair of buttons (126). Handle assembly (120) also includes a trigger (128) that is pivotable toward and away from pistol grip (124). It should be understood, however, that various other suitable configurations may be used, including but not limited to a pencil-grip configuration or a scissor-grip configuration. End effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 4.

An ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Blade (160) of the present example is operable to vibrate at ultrasonic frequencies in order to effectively cut through and seal tissue, particularly when the tissue is being clamped between clamp arm (144) and blade (160). Blade (160) is positioned at the distal end of an acoustic drivetrain. This acoustic drivetrain includes transducer assembly (112) and an acoustic waveguide (102). Transducer assembly (112) includes a set of piezoelectric discs (not shown) located proximal to a horn (not shown) of rigid acoustic waveguide (102). The piezoelectric discs are operable to convert electrical power into ultrasonic vibrations, which are then transmitted along acoustic waveguide (102), which extends through shaft assembly (130), to blade (160) in accordance with known configurations and techniques. By way of example only, this portion of the acoustic drivetrain may be configured in accordance with various teachings of various references that are cited herein.

Waveguide (102) is secured within shaft assembly (130) via a pin (133), which passes through waveguide (102) and shaft assembly (130). Pin (133) is located at a position along the length of waveguide (102) corresponding to a node associated with resonant ultrasonic vibrations communicated through waveguide (102). When ultrasonic blade (160) is in an activated state (i.e., vibrating ultrasonically), ultrasonic blade (160) is operable to effectively cut through and seal tissue, particularly when the tissue is being clamped between clamp arm (144) and ultrasonic blade (160). It should be understood that waveguide (102) may be configured to amplify mechanical vibrations transmitted through waveguide (102). Furthermore, waveguide (102) may include features operable to control the gain of the longitudinal vibrations along waveguide (102) and/or features to tune waveguide (102) to the resonant frequency of the system.

In the present example, the distal end of blade (160) is located at a position corresponding to an anti-node associated with resonant ultrasonic vibrations communicated through waveguide (102), in order to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through waveguide (102) to reach blade (160), thereby providing oscillation of blade (160) at the resonant ultrasonic frequency. Thus, when tissue is secured between blade (160) and clamp arm (144), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. While some configurations for an acoustic transmission assembly and transducer assembly (112) have been described, still other suitable configurations for an acoustic transmission assembly and transducer assembly (112) will be apparent to one or ordinary skill in the art in view of the teachings herein. Similarly, other suitable configurations for end effector (140) will be apparent to those of ordinary skill in the art in view of the teachings herein.

An operator may activate buttons (126) to selectively activate transducer assembly (112) to activate blade (160). In the present example, two buttons (126) are provided—one for activating blade (160) at a low power and another for activating blade (160) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb about pistol grip (124), position their middle, ring, and/or little finger about trigger (128), and manipulate buttons (126) using their index finger. Of course, any other suitable techniques may be used to grip and operate instrument (100); and buttons (126) may be located at any other suitable positions.

Shaft assembly (130) of the present example comprises an outer sheath (132), an inner tube (134) slidably disposed within outer sheath (132), and a waveguide (102) disposed within inner tube (134). As will be discussed in more detail below inner tube (134) is operable to translate longitudinally within outer sheath (132) relative to outer sheath (132) to selectively pivot clamp arm (144) toward and away from blade (160). Shaft assembly (130) of the present example further includes a rotation assembly (150). Rotation assembly (150) is operable to rotate the entire shaft assembly (130) and end effector (140) relative to handle assembly (120) about a longitudinal axis of shaft assembly (130). In some versions, rotation assembly (150) is operable to selectively lock the angular position of shaft assembly (130) and end effector (140) relative to handle assembly (120) about the longitudinal axis of shaft assembly (130). For instance, a rotation knob (152) of rotation assembly (150) may be translatable between a first longitudinal position, in which shaft assembly (130) and end effector (140) are rotatable relative to handle assembly (120) about the longitudinal axis of shaft assembly (130); and a second longitudinal position, in which shaft assembly (130) and end effector (140) are not rotatable relative to handle assembly (120) about the longitudinal axis of shaft assembly (130). Of course, shaft assembly (130) may have a variety of other components, features, and operabilities, in addition to or in lieu of any of those noted above. Other suitable configurations for shaft assembly (130) will be apparent to those of ordinary skill in the art in view of the teachings herein.

As shown in FIGS. 3 and 4, end effector (140) includes ultrasonic blade (160) and clamp arm (144). Clamp arm (144) includes a clamp pad (146) secured to an underside of clamp arm (144), facing blade (160). Clamp arm (144) is pivotably coupled with a distal end of outer sheath (132) of shaft assembly (130) above ultrasonic blade (160) via a pin (145). As best seen in FIG. 4, a distal end of inner tube (134) is rotatably coupled with a proximal end of clamp arm (144) below ultrasonic blade (160) via a pin (135) such that longitudinal translation of inner tube (134) causes rotation of clamp arm (144) about pin (145) toward and away from ultrasonic blade (160) to thereby clamp tissue between clamp arm (144) and ultrasonic blade (160) to cut and/or seal the tissue. In particular, proximal longitudinal translation of inner tube (134) relative to outer sheath (132) and handle assembly (120) causes clamp arm (144) to move toward ultrasonic blade (160); and distal longitudinal translation of inner tube (134) relative to outer sheath (132) and handle assembly (120) causes clamp arm (144) to move away from ultrasonic blade (160).

Figure 5:
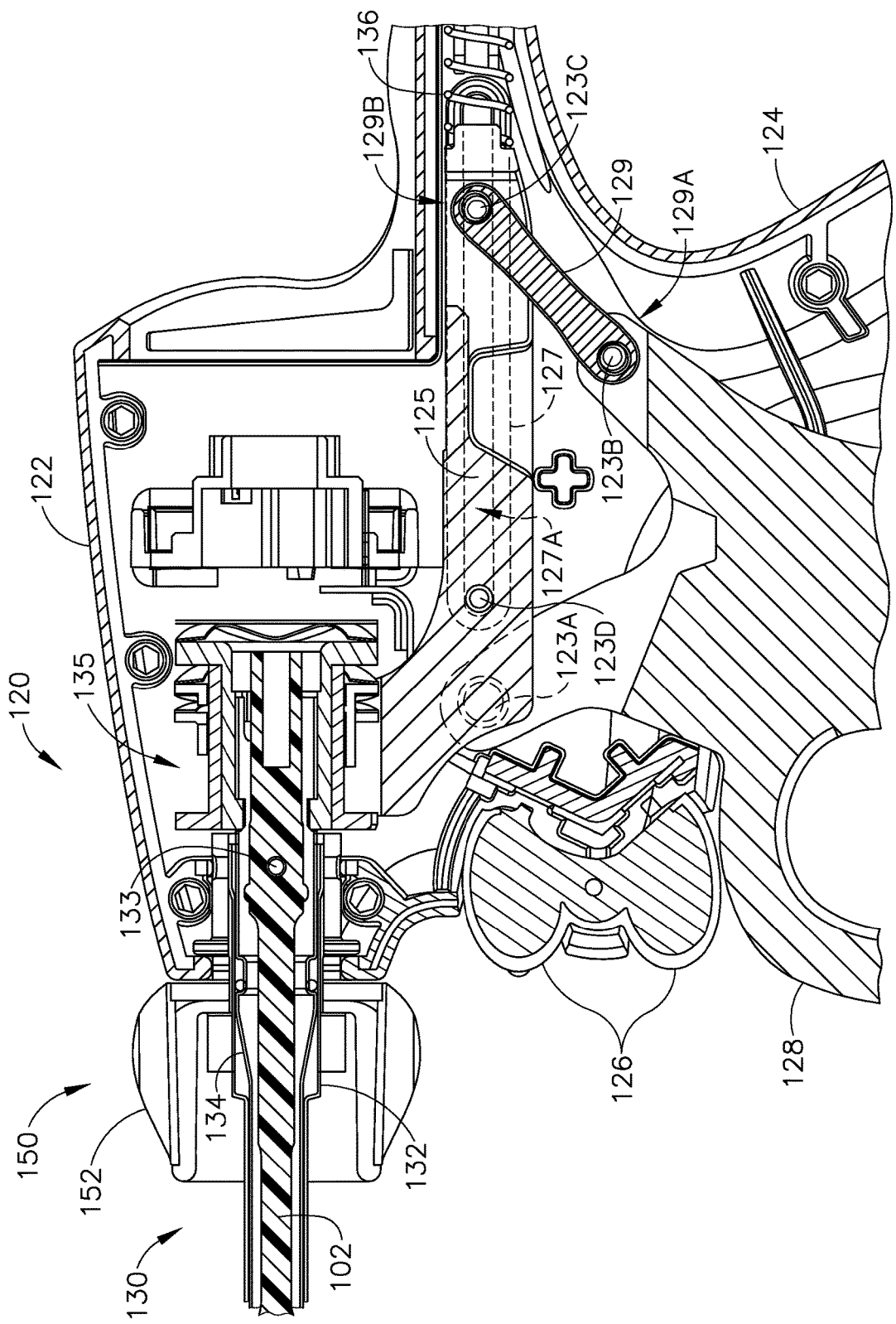
FIG. 5 depicts a cross-sectional side view of a handle assembly of the instrument of FIG. 2.

As shown in FIG. 5, and as discussed above, trigger (128) is pivotably coupled to handle assembly (120) via a pin (123A) such that trigger (128) is operable to rotate about pin (123A). As will be described in more detail below, trigger (128) is coupled with a yoke (125) via a linkage (129) such that rotation of trigger (128) about pin (123A) causes longitudinal translation of yoke (125). A first end (129A) of linkage (129) is rotatably coupled with a proximal portion of trigger (128) via a pin (123B). A second end (129B) of linkage (129) is rotatably coupled with a proximal portion of yoke (125) via a pin (123C). A pair of elongate oval-shaped projections (127) extend inwardly from interior surfaces of body (122). An interior surface of each oval-shaped projection (127) defines an elongate oval-shaped slot (127A). Pin (123C) passes completely through the proximal portion of yoke (125) and second end (129B) of linkage (129) such that ends of pin (123C) extend from opposite sides of yoke (125). These ends of pin (123C) are slidably and rotatably disposed within oval-shaped slots (127A). A pin (123D) passes completely through a distal portion of yoke (125) such that ends of pin (123D) extend from opposite sides of yoke (125). These ends of pin (123D) are slidably and rotatably disposed within oval-shaped slots (127A). It should therefore be understood that yoke (125) is longitudinally translatable within oval-shaped slots (127A) via pins (123C, 123D) between a proximal longitudinal position and a distal longitudinal position. Furthermore, because the proximal portion of trigger (128) is coupled with yoke (125) via linkage (129), pivoting of trigger (128) toward and away from pistol grip (124) will cause longitudinal translation of yoke (125) within oval-shaped slots (127A). In particular, pivoting of trigger (128) toward pistol grip (124) will cause proximal longitudinal translation of yoke (125) within oval-shaped slots (127A); and that pivoting of trigger (128) away from pistol grip (124) will cause distal longitudinal translation of yoke (125) within oval-shaped slots (127A).

A distal portion of yoke (125) is coupled with inner tube (134) of shaft assembly (130) via a coupling assembly (135). As discussed above, inner tube (134) is longitudinally translatable within outer sheath (132), such that inner tube (134) is configured to longitudinally translate concurrently with yoke (125). Furthermore, because pivoting of trigger (128) toward pistol grip (124) causes proximal longitudinal translation of yoke (125), it should be understood that pivoting of trigger (128) toward pistol grip (124) will cause proximal longitudinal translation of inner tube (134) relative to outer sheath (132) and handle assembly (120); and because pivoting of trigger (128) away from pistol grip (124) causes distal longitudinal translation of yoke (125), it should be understood that and that pivoting of trigger (128) away from pistol grip (124) will cause distal longitudinal translation of inner tube (134) relative to outer sheath (132) and handle assembly (120). Finally, because longitudinal translation of inner tube (134) causes rotation of clamp arm (144) toward and away from blade (160) as discussed above, it should be understood that pivoting of trigger (128) toward pistol grip (124) will cause clamp arm (144) to move toward ultrasonic blade (160); and that pivoting of trigger (128) away from pistol grip (124) will cause clamp arm (144) to move away from ultrasonic blade (160).

In some versions, one or more resilient members are used to bias clamp arm (144) and/or trigger (128) to the open position shown in FIG. 4. For instance, as shown in FIG. 5, a spring (136) is positioned within a proximal end of body (122) of handle assembly (120). Spring (136) bears against body (122) and a proximal end of yoke (125) to thereby bias yoke (125) toward the distal position. Biasing of yoke (125) toward the distal position causes inner tube (134) to be biased distally and further causes trigger (128) to be biased away from pistol grip (124).

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; and/or U.S. Pub. No. 2014/0114334, issued as U.S. Pat. No. 9,095,367 on Aug. 4, 2015. Additional merely illustrative variations for instrument (100) will be described in greater detail below. It should be understood that the below described variations may be readily applied to instrument (100) described above and any of the instruments referred to in any of the references that are cited herein, among others.

III. Exemplary Clamp Arm with Replaceable Clamp Pad

Those of ordinary skill in the art will recognize that clamp pad (146) may experience a substantial amount of wear and dear during use of end effector (140). For instance, clamp pad (146) may be formed of a polytetrafluoroethylene (PTFE) material. Clamp pad (146) may encounter heat, compression forces, and vibrations generated via blade (160), which may work together to eventually wear out the material forming clamp pad (146). It may therefore be desirable to provide a version of end effector (140) where clamp pad (146) is replaceable. In particular, it may be desirable to enable replacement of clamp pad (146) without necessarily also having to replace clamp arm (144) and/or other components of end effector (140).

Figure 6A:
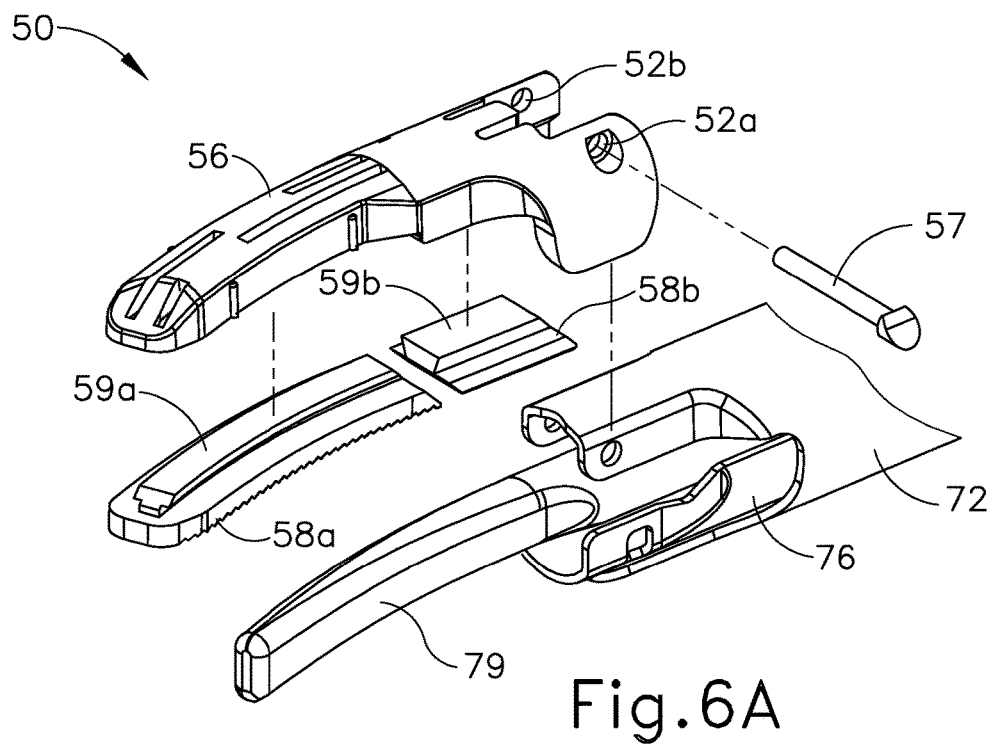
FIG. 6A depicts an exploded perspective view of an exemplary end effector that may be incorporated into the instrument of FIG. 2, with a clamp arm in a first position
Figure 6B:
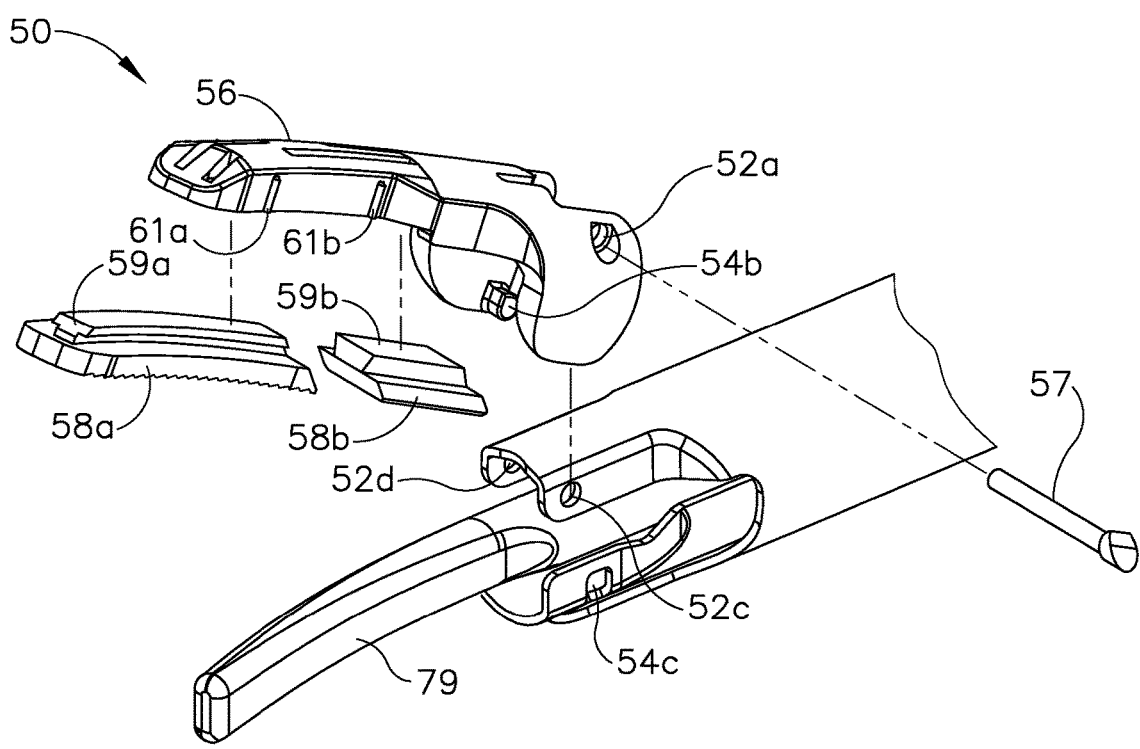
FIG. 6B depicts an exploded perspective view of the end effector of FIG. 6A, with the clamp arm in a second position.

FIGS. 6A-B show an exemplary end effector (50) with a detachable clamp arm (56) and replaceable clamp pads (58a, 58b). End effector (50) may be readily incorporated into ultrasonic instrument (20, 100) described above. End effector (50) further includes an outer sheath (72), an inner tube (76), an ultrasonic blade (79), and a pivot pin (57). Outer sheath (72), inner tube (76), and blade (79) are substantially similar to outer sheath (132), inner tube (134) and ultrasonic blade (160), respectively, discussed above.

Detachable clamp arm (56) includes coupling holes (52a, 52b) that are configured to receive pivot pin (57). Clamp arm (56) is pivotally coupled to outer sheath (72) via pivot pin (57). Clamp arm (56) is pivotally coupled to inner sheath (76) via integral studs (54b), which are disposed in openings (54c) of inner sheath (76). Clamp pads (58a, 58b) further include tapered tenons (59a, 59b) that are configured to mate with complementary mortises (not shown) defined by detachable clamp arm (56). Tenons (59a, 59b) are configured to slide within mortises (not shown) at the proximal end of clamp arm (56) when clamp arm (56) is detached from outer sheath (72). Therefore, when clamp arm (56), with assembled clamp pads (58a, 58b), is attached to outer sheath (72) via pivot pin (57), pivot pin (57) prevents clamp pads (58a, 58b) from sliding proximally relative to clamp arm (56). In other words, pivot pin (57) and the closed distal end of clamp arm (56) confine clamp pads (58a, 58b) within the mortise via tenons (59a, 59b), with pivot pin (57) and the closed distal end of clamp arm (56) cooperating to act as longitudinal stops.

When detachable clamp arm (56) is assembled to outer sheath (72), clamp pads (58a, 58b) may be fixed relative to clamp arm (56). However, after a surgical procedure, clamp pads (58a, 58b) may be removed from detachable clamp arm (56) by removing pivot pin (57) to decouple clamp arm (56) and outer sheath (72). Once pivot pin (57) is removed from coupling holes (52a, 52b), clamp arm (56) may be removed from outer sheath (72), which enables clamp pads (58a, 58b) to slide relative to clamp arm (56) in the proximal direction. Used clamp pads (58a, 58b) may then be removed and replaced with new clamp pads (58a, 58b) with similar qualities. Then, assembled clamp arm (56) with new clamp pads (58a, 58b) may be coupled to outer sheath (72) via pivot pin (57), thereby fixing clamp pads (58a, 58b) relative to clamp arm (56). By way of example only, end effector (50) may be further constructed and operable in accordance with at least some of the teachings of U.S. Pat. No. 7,544,200, entitled "Combination Tissue Pad for Use with an Ultrasonic Surgical Instrument," issued Jun. 9, 2009, the disclosure of which is incorporated by reference herein.

IV. Exemplary Alternative Replaceable Clamp Pads

While end effector (50) allows for replacement of clamp pads (58a, 58b), end effector (50) requires removal of clamp arm (56) from outer sheath (72) in order to replace clamp pads (58a, 58b). In some instances, it may be desirable to allow for replacement of a clamp pad (58a, 58b, 146) from a clamp arm (56, 144) without having to first remove the clamp arm (56, 144) from anything. Providing replacement of a clamp pad (58a, 58b, 146) from a clamp arm (56, 144) without having to first remove the clamp arm (56, 144) from anything may simplify the process of sterilizing the instrument (20, 100), thereby saving time and/or costs associated with replacing clamp pad (58a, 58b, 146). The following examples relate to various alternative clamp arm and clamp pad configurations that may be used to provide replacement of the clamp pad without having to first remove the clamp arm from anything else. It should be understood that the following examples may be readily incorporated into end effectors (50, 140). It should also be understood that the following examples are merely illustrative.

In any of the examples described below, instrument (100) may be further modified in accordance with at least some of the teachings of U.S. patent application Ser. No. 14/623,812, entitled "Ultrasonic Surgical Instrument with Removable Handle Assembly," filed Feb. 17, 2015, issued as U.S. Pat. No. 10,010,340 on Jul. 3, 2018, the disclosure of which is incorporated by reference herein. For instance, instrument (100) may be modified to enable clamp arm (144) to be hyperextended to pivot wider than the open position shown in FIG. 4, as disclosed in U.S. patent application Ser. No. 14/623,812, issued as U.S. Pat. No. 10,010,340 on Jul. 3, 2018 (see, e.g., FIGS. 36A-36B and associated text of U.S. patent application Ser. No. 14/623,812, issued as U.S. Pat. No. 10,010,340 on Jul. 3, 2018). Such hyperextension of clamp arm (144) may provide easier access to clamp pad (146) and thereby further facilitate replacement of clamp pad (146).

In addition or in the alternative, in any of the examples described below, instrument (100) may be further modified in accordance with at least some of the teachings of U.S. patent application Ser. No. 14/553,378, entitled "Ultrasonic Surgical Instrument with Blade Cooling through Retraction," filed Nov. 25, 2014, issued as U.S. Pat. No. 10,433,863 on Oct. 8, 2019, the disclosure of which is incorporated by reference herein. For instance, instrument (100) may be modified to enable blade (160) to be retracted proximally from the position shown in FIG. 4, as disclosed in U.S. patent application Ser. No. 14/553,378, issued as U.S. Pat. No. 10,433,863 on Oct. 8, 2019, (see, e.g., FIGS. 20A-20B and associated text of U.S. patent application Ser. No. 14/553,378, issued as U.S. Pat. No. 10,433,863 on Oct. 8, 2019). Such retraction of blade (160) may also provide easier access to clamp pad (146) and thereby further facilitate replacement of clamp pad (146) in accordance with the teachings below.

As yet another merely illustrative example, the various teachings below may be combined with the various teachings of U.S. patent application Ser. No. 14/552,614, entitled "Ultrasonic Surgical Instrument with Staged Clamping," filed Nov. 25, 2014, issued as U.S. Pat. No. 10,004,527 on Jul. 26, 2018, the disclosure of which is incorporated by reference herein. It should be understood that a replaceable clamp pad (146) may have various kinds of features that may fit into grooves of a clamp arm (144) and/or otherwise fit with features of a clamp arm (144). Various suitable ways in which the below teachings may be implemented into various kinds of instruments (100) will be apparent to those of ordinary skill in the art.

A. Exemplary Clamp Arm with Complementary Clamp Pad Having T-Slot

Figure 7:
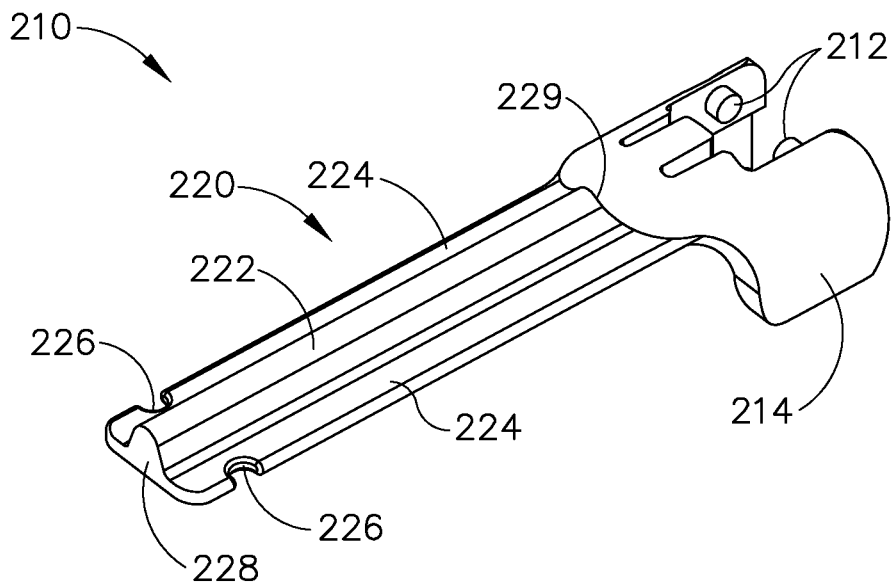
FIG. 7 depicts a perspective view of an exemplary alternative clamp arm that may be incorporated into the end effector of FIG. 3.

FIGS. 7-10 show an exemplary alternative clamp arm assembly (200) and related components that may be readily incorporated into end effector (50, 140) in place of clamp arm (56, 144) and clamp pad (58a, 58b, 146). Clamp arm assembly (200) of this example comprises a clamp arm (210) and a clamp pad (250). As best seen in FIG. 7, clamp arm (210) includes a proximal portion (214) and an elongated distal portion (220). Proximal portion (214) includes coupling members (212) that are configured to pivotally couple with outer sheath (72, 132) or inner tube (76, 134) as described above. Elongated distal portion (220) includes a proximal end (229), a distal end (228), a pair of inwardly extending mating recesses (226), and a T-shaped cross-section defined by flattened surfaces (224) and an elongated rib (222) extending from proximal end (229) to distal end (228). Elongated distal portion (220) is configured to receive clamp pad (250) at distal end (228), which may eliminate the need for clamp arm (210) to be removed from the rest of instrument (20, 100) in order to install clamp pad (250).

Figure 8:
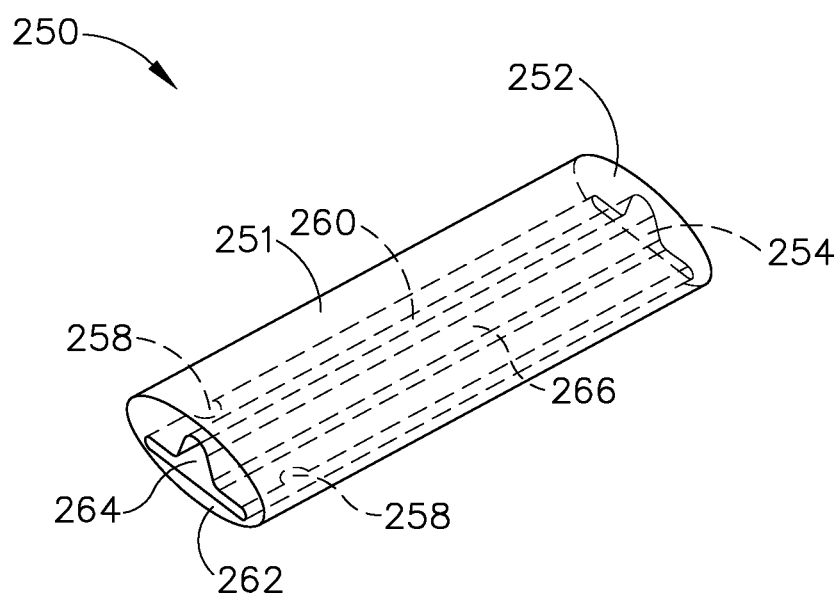
FIG. 8 depicts a perspective view of an exemplary replaceable clamp pad that may be used with the clamp arm of FIG. 7.

As best seen in FIG. 8, clamp pad (250) includes a proximal face (252) defining a proximal opening (254), a distal face (262) defining a distal opening (264), an exterior surface (251) defining a complementary sleeve (266) and a complementary elongated slot (260), both of which extend from proximal opening (254) to distal opening (264). Clamp pad (250) further includes a pair of complementary mating nubs (258) that are positioned to correspond with mating recesses (226) of clamp arm (210) when clamp pad (250) is fully seated on clamp arm (210).

Figure 9:
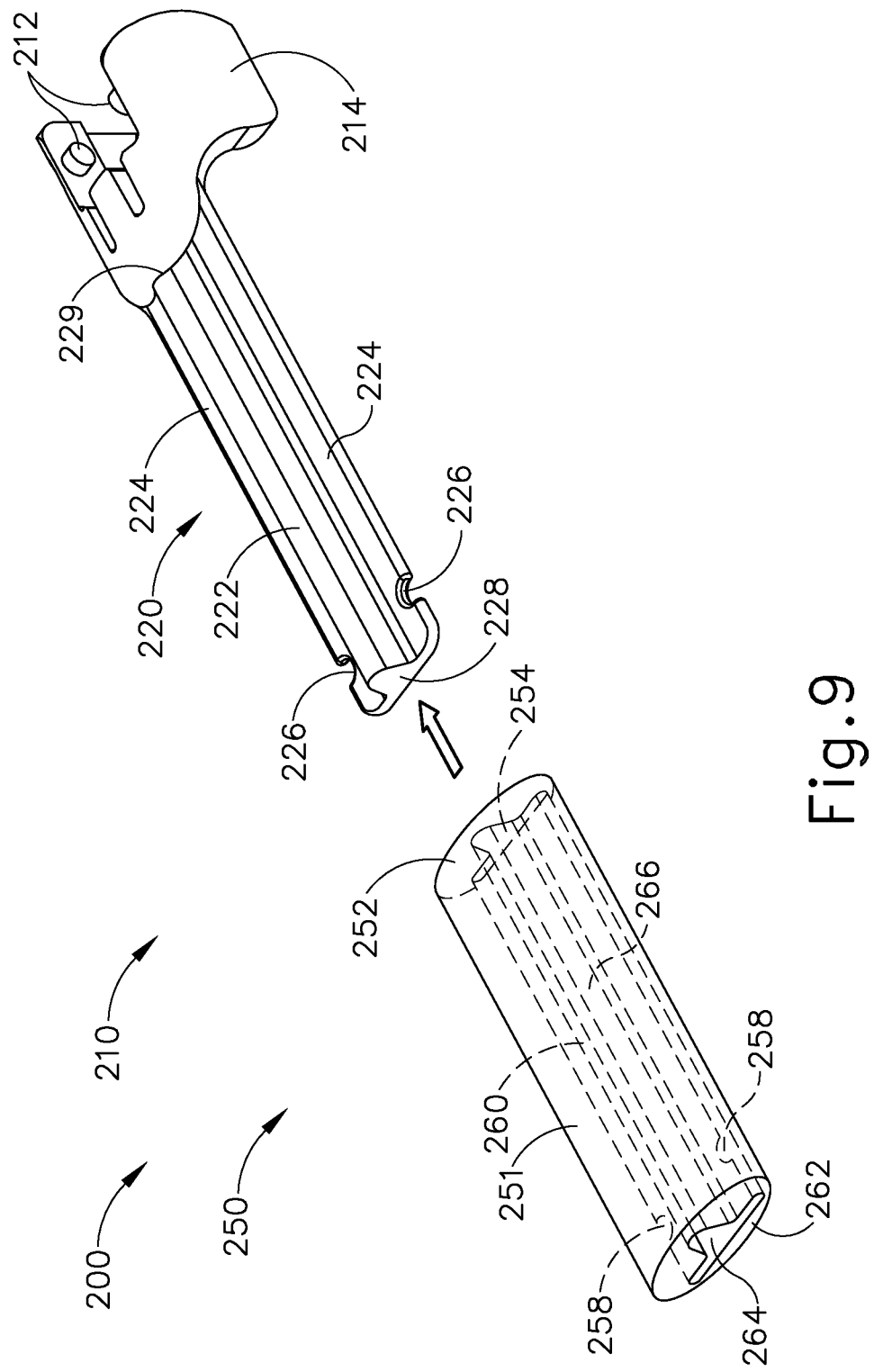
FIG. 9 depicts a perspective view of the clamp pad of FIG. 8 being attached to the clamp arm of FIG. 7.

As shown in FIG. 9, proximal opening (254) of clamp pad (250) is configured to receive distal end (228) of clamp arm (210). The cross-sectional area of proximal opening (254) and distal opening (264) are defined by complementary sleeve (266) and complementary elongated slot (260). Complementary sleeve (266) and complementary elongated slot (260) are dimensioned to complement elongated flattened surfaces (224) and elongated rib (222), respectively. This complementary T-shaped configuration prevents clamp pad (250) from rotating about the longitudinal axis defined by elongated distal portion (220) of clamp arm (210) once clamp pad (250) is fitted around clamp arm (210). Additionally, the complementary T-shaped configuration ensures that clamp pad (250) will mate with clamp arm (210) in a predefined orientation such that the portion of exterior surface (251) that is configured to compress tissue against blade (24, 79, 160) consistently faces the appropriate direction each time clamp pad (250) is replaced.

In addition to preventing rotation of clamp pad (250) about the longitudinal axis defined by elongated distal portion (220) of clamp arm (210), mating recesses (226) of clamp arm (210) and complementary mating nubs (258) of clamp pad (250) are configured to mate with each other once clamp pad (250) is placed in its desired location relative to clamp arm (210). Mating recesses (226) and mating nubs (258) may be configured to provide a snap fit. Thus, mating nubs (258) may slightly deform around distal end (228) of clamp arm (210) until nubs (258) reach mating recesses (226). Nubs (258) may then snap into place within mating recesses (226). Once nubs (258) and mating recesses (226) are longitudinally aligned, clamp pad (250) is substantially prevented from inadvertently translating along the longitudinal axis defined by elongated distal portion (220). However, an operator may still remove clamp pad (250) for replacement by providing a sufficient distally oriented force on clamp pad (250) as clamp arm (210) is held stationary.

Figure 10:
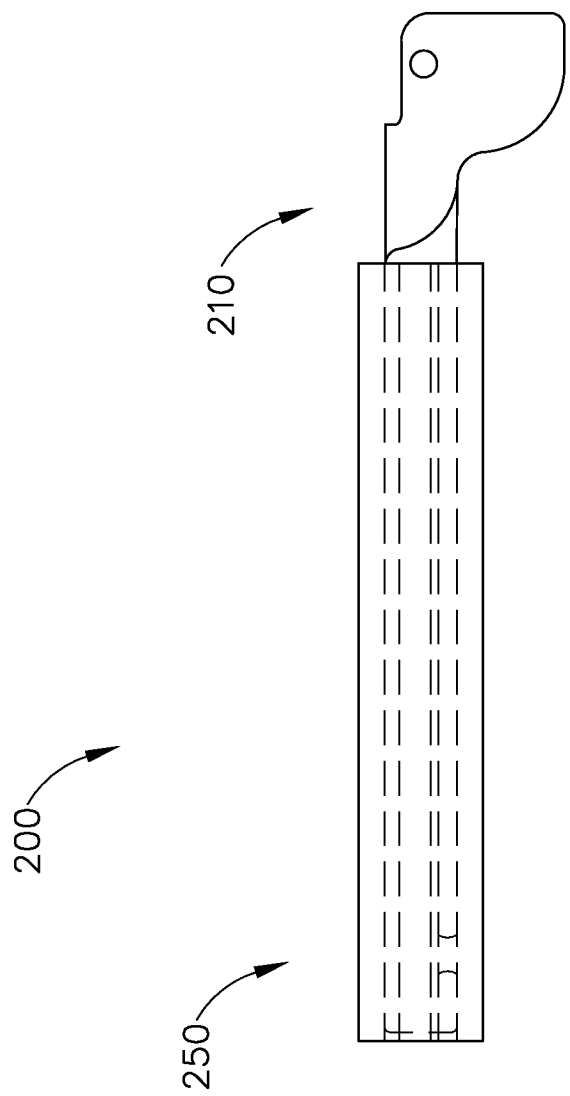
FIG. 10 depicts a side elevational view of the exemplary clamp pad of FIG. 8 attached to the clamp arm of FIG. 7.

As shown in FIG. 10, with clamp pad (250) unable to rotate or translate about the longitudinal axis defined by elongated distal portion (220) of clamp arm (210), clamp pad (250) is substantially fixed relative to clamp arm (210). Therefore, clamp pad (250) may be installed on clamp arm (210) without needing to first decouple clamp arm (210) from the rest of instrument (20, 100). Likewise, a spent clamp pad (250) may be removed from clamp arm (210) without needing to first decouple clamp arm (210) from the rest of instrument (20, 100).

Various kinds of materials may be used to form clamp pad (250). By way of example only, at least an upper portion of clamp pad (250) may be formed of a polymeric material that is resilient and/or elastomeric to assist in gripping onto clamp arm (210). In addition, at least the portion of clamp pad (250) that will contact tissue and compress the tissue against blade (24, 79, 160) during use of clamp arm assembly (200) may comprise polytetrafluoroethylene. Various other suitable materials and combinations of materials that may be used to form clamp pad (250) and different regions thereof will be apparent to those of ordinary skill in the art in view of the teachings herein.

Figure 11:
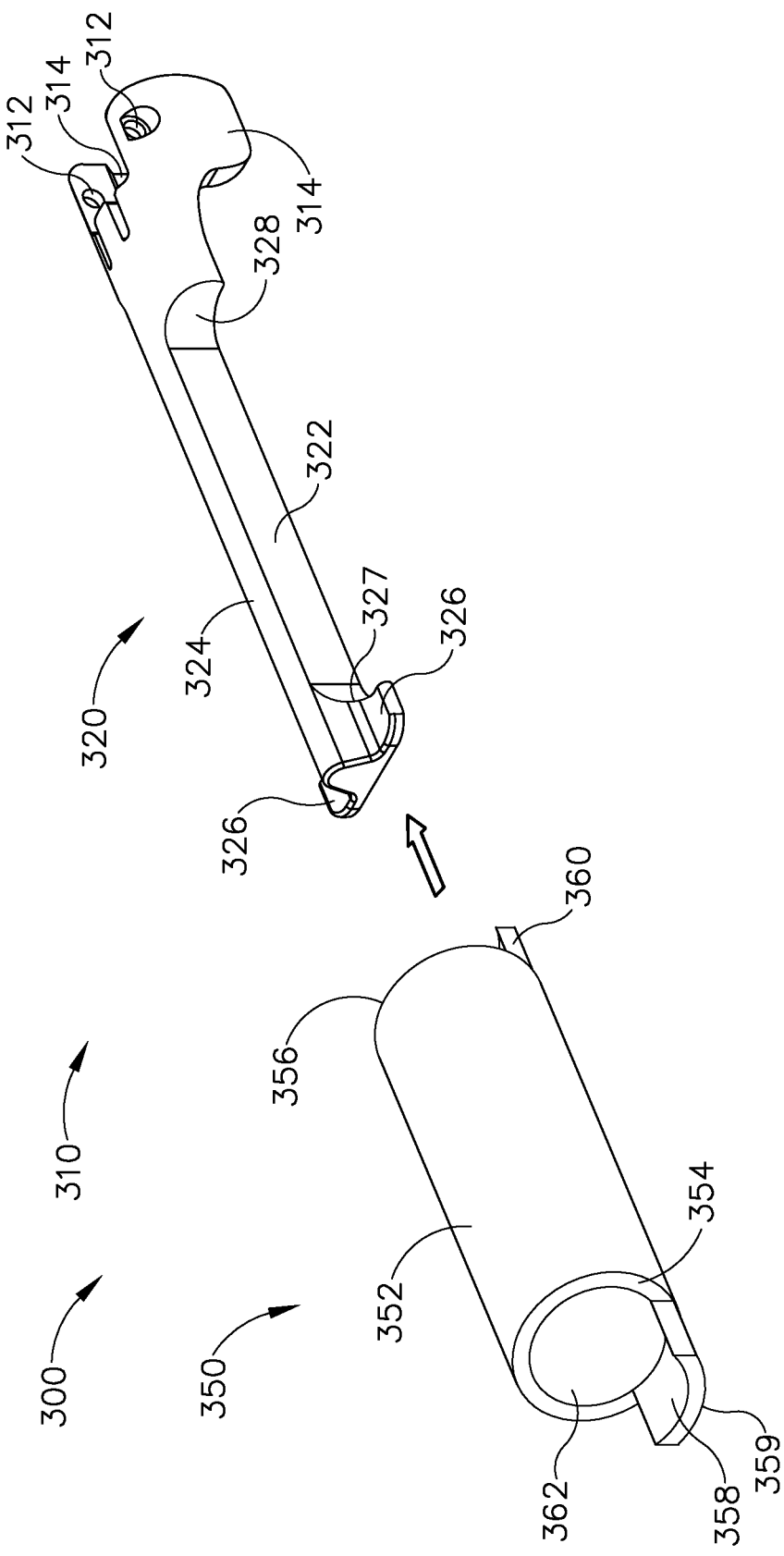
FIG. 11 depicts a perspective view of an exemplary alternative clamp arm assembly that may be incorporated into the end effector of FIG. 3, with a clamp pad separated from a clamp arm.

B. Exemplary Clamp Arm with Cylindraceous Elastomeric Clamp Pad and Removal Instrument FIGS. 11-12B show another exemplary alternative clamp arm assembly (300) and related components that may be readily incorporated into end effector (50, 140) in place of clamp arm (56, 144) and clamp pad (58a, 58b, 146). Clamp arm assembly (300) of this example includes a clamp arm (310) and an elastomeric clamp pad (350). Clamp arm (310) includes a proximal portion (314) and an elongated distal portion (320). Proximal portion (214) includes coupling members (312) that are configured to pivotally couple with outer sheath (72, 132) or inner tube (76, 143) as described above. Elongated distal portion (320) includes a proximal stop (328), a distal stop (327), a protruding head (326), a flattened surface (324), and a narrowed portion (322). Flattened surface (324) and narrowed portion (322) both extend from proximal stop (328) to distal stop (327). As described in greater detail below, elongated distal portion (320) is dimensioned to receive and mate with elastomeric clamp pad (350).

Clamp pad (350) includes a proximal face (356), a distal face (354), an exterior surface (352), an elongated channel (362) extending from proximal face (356) to distal face (354), a distal base (358) extending distally from distal face (354), a proximal base (360) extending proximally from proximal face (356), and a contact portion (359) that is partially defined by proximal base (360), distal base (358), and exterior surface (352).

As shown in FIG. 11, elongated channel (362) is configured to receive protruding head (326) of elongated distal portion (320) at proximal face (356) of clamp pad (350). This may eliminate the need for clamp arm (310) to be decoupled from the rest of from the rest of instrument (20, 100) in order to install or replace clamp pad (350). Protruding head (326) is dimensioned to be larger than the cross-sectional area of elongated channel (362). In other words, head (326) has a width that exceeds the inner diameter of channel (362). In the present example, elastomeric clamp pad (350) is formed of a resilient material that allows stretching to an expanded configuration but provides a bias toward a contracted configuration. Therefore, as proximal face (356) is placed over protruding head (326), protruding head (326) enlarges the dimensions of elongated channel (362), allowing clamp pad (350) to slide over elongated distal portion (320). Contact between protruding head (326) and the inner sidewall of channel (362) creates a frictional braking force, which may lead to some resistance of clamp pad (350) sliding over elongated distal portion (320).

Elongated distal portion (320) and elongated channel (362) are dimensioned such that protruding head (326) will exit elongated channel (362) at distal face (354) once elongated distal portion (320) has completely received clamp pad (350) as shown in FIG. 12B. Once protruding head (326) has traveled through elongated channel (362), elongated channel (362) resiliently contracts to recover to its original dimensions. At this stage, distal stop (327) of clamp arm (310) prevents clamp pad (350) from traveling distally in relation to clamp arm (310). In other words, distal stop (327) provides a stop that substantially prevents clamp pad (350) from traveling distally from clamp arm (320). Similarly, proximal stop (328) is positioned to engage proximal face (356) when clamp pad (350) is in its final position, thereby preventing clamp pad (350) from traveling proximally in relation to clamp arm (310). As such, clamp pad (350) is substantially incapable of translating along the longitudinal axis as defined by elongated distal portion (320) once clamp pad (350) is fully seated on clamp arm (310). However, an operator may still remove clamp pad (350) for replacement by providing a sufficient distally oriented force on clamp pad (350) as clamp arm (310) is held stationary, as will be described in greater detail below.

Flattened surface (324) and narrowed portion (322) define a cross sectional area that is configured to mate with elongated channel (362). In addition to (or as an alternative to) stops (327, 328) cooperating to secure clamp pad (350) relative to clamp arm (310), flattened surface (324) and narrowed portion (322) may be dimensioned to provide an interference fit with elongated channel (362). Such an interference fit may further secure clamp pad (350) relative to clamp arm (310). Alternatively, flattened surface (324) and narrowed portion (322) may provide any other suitable fit with elongated channel (362).

Distal base (358) and proximal base (360) are dimensioned to mate with the underside of protruding head (326) and the underside of proximal stop (328) respectively. Both bases (358, 360) have arched faces that mate with protruding head (326), and proximal stop (328) respectively. Engagement between bases (358, 360) and protruding head (326) and proximal stop (328) prevents tube pad (320) from rotating about the longitudinal axis defined by elongated distal portion (320) of clamp arm (310) once clamp pad (350) is fully seated on clamp arm (310). Additionally, bases (358, 360) mating with protruding head (326) and proximal stop (328) ensures that clamp pad (350) will consistently mate with clamp arm (310) with a predefined orientation such that the portion of exterior surface (352) that is configured to compress tissue against blade (24, 79, 160) consistently faces the appropriate direction each time clamp pad (350) is replaced. Of course, other mating features could be utilized to prevent rotation of clamp pad (350) about the longitudinal axis defined by elongated distal portion (320) and to provide angular indexing that ensures consistent mating of clamp arm (310) and clamp pad (350).

As shown in FIG. 12B, with clamp pad (350) unable to rotate or translate about the longitudinal axis defined by elongated distal portion (320) of clamp arm (310), clamp pad (350) is substantially fixed relative to clamp arm (310). Therefore, clamp pad (350) may be installed on clamp arm (310) without needing to first decouple clamp arm (310) from the rest of instrument (20, 100). Likewise, a spent clamp pad (350) may be removed from clamp arm (310) without needing to first decouple clamp arm (310) from the rest of instrument (20, 100).

Various kinds of materials may be used to form clamp pad (350). By way of example only, at least an upper portion of clamp pad (350) may be formed of a polymeric material that is resilient and/or elastomeric to assist in gripping onto clamp arm (310). In addition, at least the portion of clamp pad (350) that will contact tissue and compress the tissue against blade (24, 79, 160) during use of clamp arm assembly (300) may comprise polytetrafluoroethylene. Various other suitable materials and combinations of materials that may be used to form clamp pad (350) and different regions thereof will be apparent to those of ordinary skill in the art in view of the teachings herein.

Figure 13:
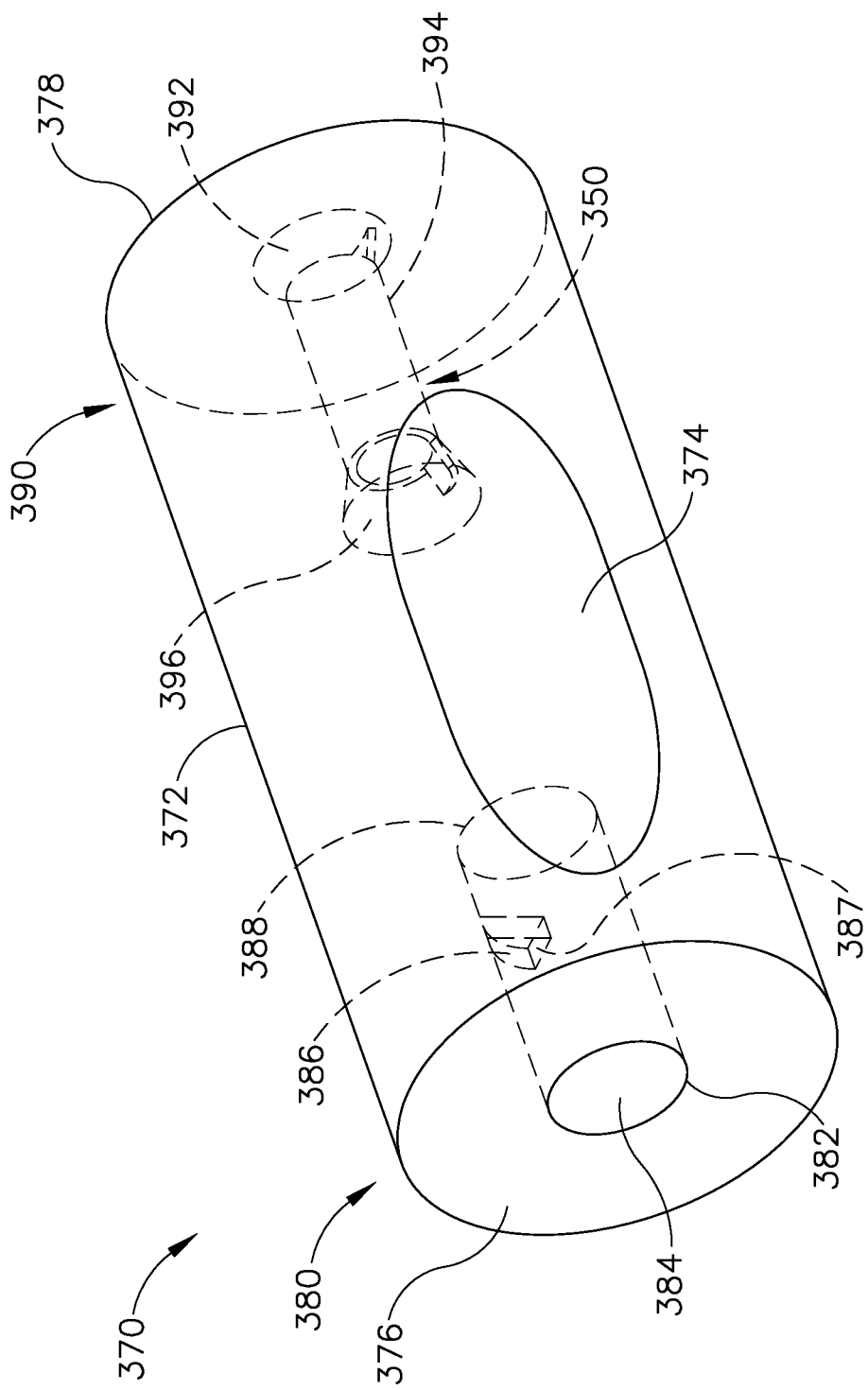
FIG. 13 depicts a perspective view of an exemplary clamp pad removal instrument.
Figure 14:
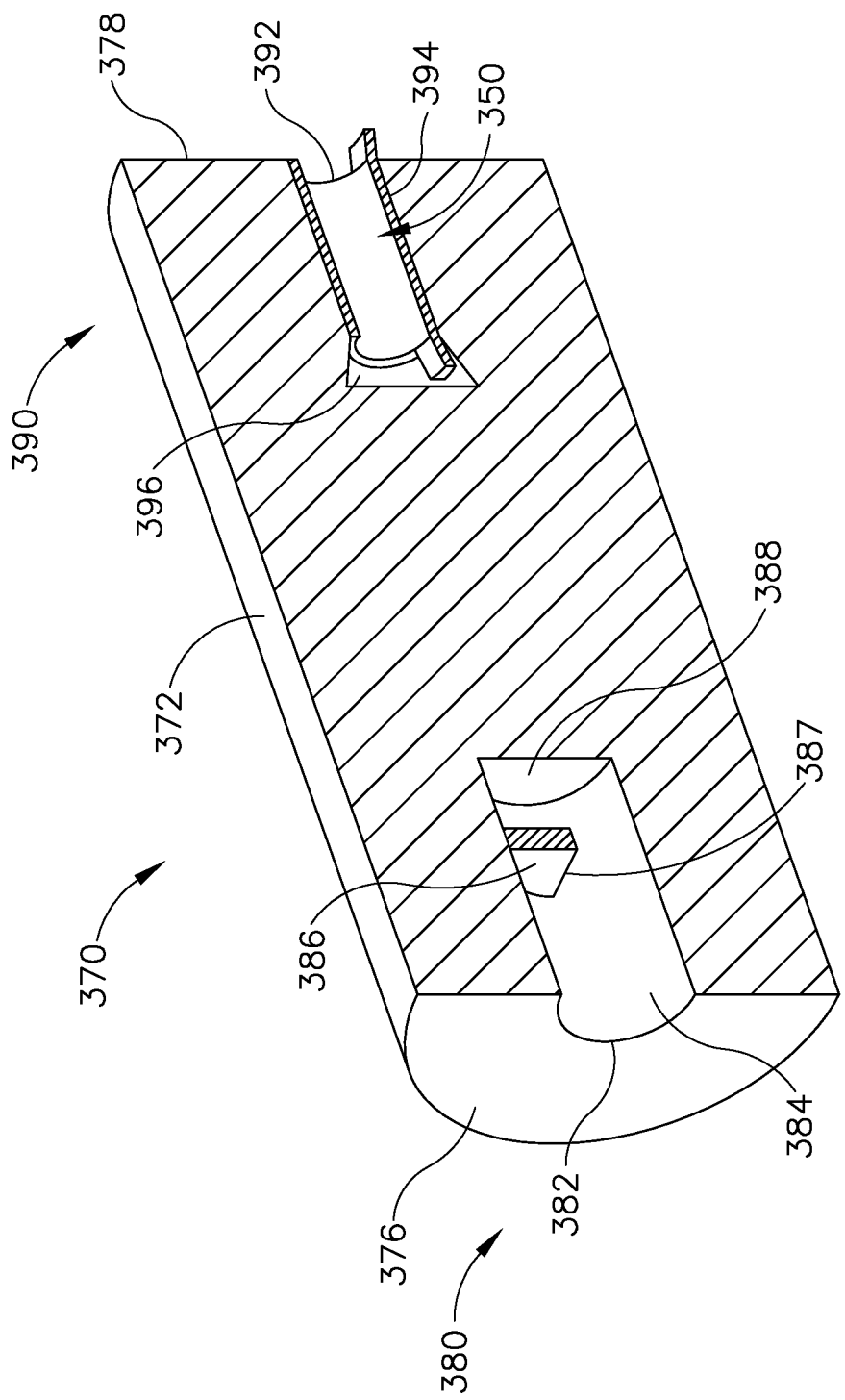
FIG. 14 depicts a cross-sectional perspective view of the instrument of FIG. 13.
Figure 21:
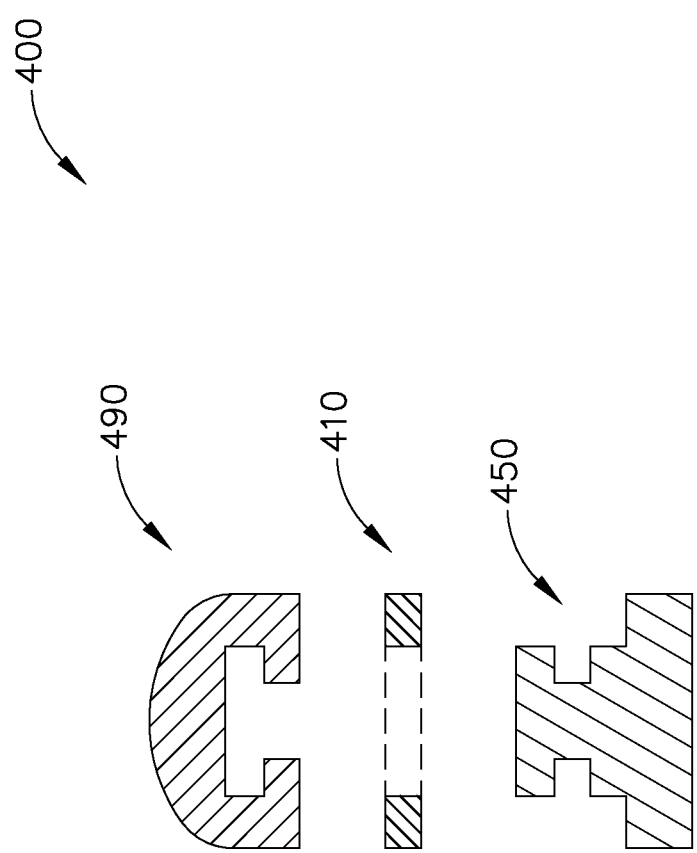
FIG. 21 depicts a cross-sectional view of the sliding lock of FIG. 15, the clamp arm of FIG. 16, and the clamp pad of FIG. 17 separated from each other.

FIGS. 13-14 show an exemplary instrument (370) that may be used to install and remove clamp pad (350) to and from clamp arm (310). Instrument (370) of this example includes an exterior surface (372) defining a grip (374), a pad installation portion (390), and a pad removal portion (380). Grip (374) is designed to allow an operator to easily handle instrument (370) while either installing or removing pad (350) onto or from clamp arm (310). Grip (374) may have any suitable texture, surface treatment, and/or configuration as will be apparent to one having ordinary skill in the art in view of the teachings herein. In the present example, instrument (370) is described as being used with clamp pad (350) and clamp arm (310), though it should be understood that instrument (370) may be readily modified for use with clamp pad (250) and clamp arm (210) or any other kind of clamp pad that provides a snap fit or interference fit with a corresponding clamp arm.

Pad installation portion (390) includes an installation face (378), an installation entry (392), an installation tube (394) configured to house clamp pad (350), and an installation stop (396) dimensioned to receive protruding head (326) of clamp arm (310) once clamp pad (350) is completely installed. Instrument (370) allows an operator to utilize grip (374) to place installation entry (392) directly above clamp arm (310). With clamp pad (350) already in installation tube (394), an operator may utilize instrument (370) to develop a sufficient grip required to distribute the force required to allow protruding head (326) to travel through elongated channel (362). Once protruding head (326) snaps is located in its final position relative to clamp pad (350) as described above, protruding head (326) will enter installation stop (396). At this point, an operator may pull instrument (370) away from clamp arm (310). Since protruding head (326) has been positioned distal to clamp pad (350), protruding head (326) will carry clamp pad (350) with clamp arm (310) due to interaction between protruding head (326) and distal face (354).

Pad removal portion (380) includes a removal face (376), a removal entry (382), a removal channel (384) configured to receive clamp pad (350) already installed on clamp arm (310), a removal stop (388), a blade fixture (386) fixed within removal channel (384), and a blade (387) attached to blade fixture (386). Instrument (370) allows an operator to utilize grip (374) to place removal entry (382) directly above clamp arm (310). With clamp pad (350) already installed on clamp arm (310), an operator may utilize instrument (370) to insert clamp pad (350) and clamp arm (310) into removal channel (384). Blade (387) is positioned on blade fixture (386) to make contact with clamp pad (350) as clamp pad (350) and clamp arm (310) travel within removal channel (384) toward removal stop (388). Blade (387) is positioned to engage clamp pad (350) but not engage clamp arm (310).

In the present example, blade (387) is configured to engage clamp pad (350) in such a manner to retain clamp pad (350) in removal channel (384). In particular, when the operator inserts clamp arm assembly (300) into removal channel (384) and then pulls clamp arm (310) from removal channel (384), clamp pad (350) remains disposed in channel (384) due to engagement with blade (387). In the present example, blade (386) is oriented along a plane that is perpendicular to the longitudinal axis of removal channel (384). In some other versions, blade (386) is oriented along a plane that is obliquely oriented relative to the longitudinal axis of removal channel (384). It should also be understood that blade (386) may be configured to pivot or deflect distally as clamp arm assembly (300) is inserted into removal channel (384); yet not pivot or deflect proximally as clamp arm (310) is pulled proximally from removal channel (384). Blade (386) may thus act as a pawl, providing just one-way movement of clamp pad (350) in removal channel (384) to retain clamp pad (350) in channel (384) by snagging clamp pad (350) in channel.

As yet another merely illustrative variation, blade (387) may be configured to sever at least a portion of clamp pad (350) as clamp arm assembly (300) is inserted into removal channel (384). In some such versions, blade (387) is oriented along a plane that is parallel with the longitudinal axis of removal channel (384). It should be understood that severing at least a portion of clamp pad (350) may relax a grip that clamp pad (350) might otherwise have on clamp arm (310), thereby promoting removal of clamp pad (350) from clamp arm (310). In addition or in the alternative, severing at least a portion of clamp pad (350) may effectively enlarge channel (362) in clamp pad (350), facilitating the passage of head (326) through channel (362) as clamp arm (310) is pulled proximally relative to clamp pad (350). In at least some versions where at least a portion of clamp pad (350) is severed, clamp arm (310) may be removed from channel (384) with the severed clamp pad (350) still coupled with clamp arm (310), such that the operator must then peel or otherwise remove the severed clamp pad (350) from clamp arm (310). Other structural features that may be incorporated into instrument (370) to facilitate removal of clamp pad (350) from clamp arm (310) will be apparent to those of ordinary skill in the art in view of the teachings herein.

In an exemplary use of instrument (370), an operator may use pad removal portion (380) to remove a spent clamp pad (350) as described above, then simply rotate instrument (370) 180° to orient pad installation portion (390) toward clamp arm (310). The operator may then use pad installation portion (390) to install a replacement clamp pad (350) on clamp arm (310) as described above. It should therefore be understood that instrument (370) may be used to remove and replace a clamp pad (350) on the same clamp arm (310) in a single procedure.

C. Exemplary Alternative Clamp Arm with Three Piece Clamp Arm Assembly

FIGS. 15-22D show another exemplary clamp arm assembly (400) and related components that may be readily incorporated into end effector (50, 140) in place of clamp arm (56, 144) and clamp pad (58a, 58b, 146). Clamp arm assembly (400) of this example includes a clamp arm (410), a clamp pad (450), and a sliding lock (490). As will be described in greater detail below, clamp pad (450) may be inserted from the underside of clamp arm (410), and then sliding lock (490) may be slid from the top of clamp arm (410) in the proximal direction to fix replaceable clamp pad (450) in relation to clamp arm (410).

As shown in FIG. 16, clamp arm includes a frame (416), bridging members (418), a proximal portion (414), and a distal portion (420). Frame and bridging members (418) define openings (422) that accommodate inserted portions of clamp pad (450) as will be described in greater detail below.

As shown in FIG. 17 and FIG. 20, clamp pad (450) includes a pad portion (452) that is configured to be positioned under frame (416) and a mating portion (454) that is configured to be positioned through and above openings (422). Mating portion (454) further includes a frame engagement portion (458), a narrow lock engagement portion (457), and a wide lock engagement portion (456). Frame engagement portion (458) and pad portion (452) help define frame channel (462), where frame (416) is housed. Frame engagement portion (458), narrow lock engagement portion (457), and wide lock engagement portion (456) define locking channel (460), which sliding lock (490) engages in order to fix clamp pad (450) relative to clamp arm (410).

As shown in FIG. 18, sliding lock (490) includes a cap (492) and two arms (494) extending inwardly from cap (492). The interior of cap (492) and arms (494) define T-shaped slot (496). T-shaped slot (496) is configured to mate with wide lock engagement portion (456) and narrow lock engagement portion (457) to fix replaceable clamp pad (450) relative to clamping arm (410).

Figure 22D:
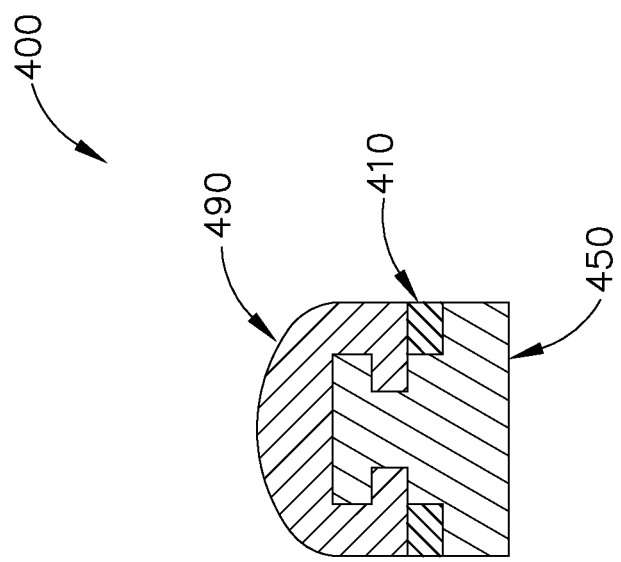
FIG. 22D depicts a cross-sectional view of the sliding lock of FIG. 15, the clamp arm of FIG. 16, and the clamp pad of FIG. 17 secured together.

FIGS. 22A-D show how exemplary clamp arm assembly (400) is assembled. As mentioned above, first replaceable clamp pad (450) is inserted from the underside of clamp arm (410). As such, each mating portion (454) extends through and above a respective opening (422) defined by frame (416) and bridging members (418) of clamp arm (410). At this point, as shown in FIG. 22B, frame (416) is located within frame channel (462) as defined by frame engagement portion (458) and pad portion (452). As can also be seen in FIGS. 22B-22C, narrow lock engagement portion (457) and wide lock engagement portion (456) extend above opening (422) defined by frame (416) and bridging members (416). It should be noted that narrow lock engagement portion (457) and wide lock engagement portion (456) define a complementary T-shaped rail that is configured to mate with T-shaped slot (496) defined by cap (492) and arms (494) of sliding lock (490). Therefore, sliding lock (490) may slide in the proximal direction, with arms (494) of sliding lock (490) engaging locking channel (460), allowing T-shaped slot (496) to mate with both narrow lock engagement portion (457) and wide lock engagement portion (456) as shown in FIG. 22D. As a result, replaceable clamp pad (450) is locked between the confines of frame (416) of clamp arm (410) and T-slot (496) of sliding lock (490), preventing replaceable clamp pad (450) from further movement relative to clamp arm (410). While narrow lock engagement portion (457) and wide lock engagement portion (456) define a T-shaped rail to mate with T-shaped slot (496) in the present example, any number of suitable geometries may used to mate sliding lock (490) with mating portion (454) or replaceable clamp pad (450), such as but not limited to, a dovetail slot or any other connecting method apparent to one having ordinary skill in the art in view of the teachings herein.

Sliding lock (490) may provide a snap fit with either distal portion (420) or proximal portion (414) of clamp arm (410), preventing inadvertent longitudinal translation of replaceable clamp pad (450) relative to clamp arm (410). As another merely illustrative example, detents may be used to selectively retain the longitudinal position of sliding lock (490) relative to clamp arm (410). Of course, any other suitable structures or methods may be used to selectively retain the longitudinal position of sliding lock (490) relative to clamp arm (410) as will be apparent to one having ordinary skill in the art in view of the teachings herein. It should also be understood that the fit between sliding lock (490) and clamp arm (410) may nevertheless permit an operator to intentionally remove sliding lock (490) from clamp arm (410) in order to replace a spent clamp pad (450).

Various kinds of materials may be used to form clamp pad (450). By way of example only, at least an upper portion of clamp pad (350) may be formed of a polymeric material that is rigid to maintain secure engagement with sliding lock (490). In addition, at least the portion of clamp pad (450) that will contact tissue and compress the tissue against blade (24, 79, 160) during use of clamp arm assembly (400) may comprise polytetrafluoroethylene. Various other suitable materials and combinations of materials that may be used to form clamp pad (450) and different regions thereof will be apparent to those of ordinary skill in the art in view of the teachings herein.

D. Threaded Clamp Arm and Threaded Replaceable Pad

Figure 23:
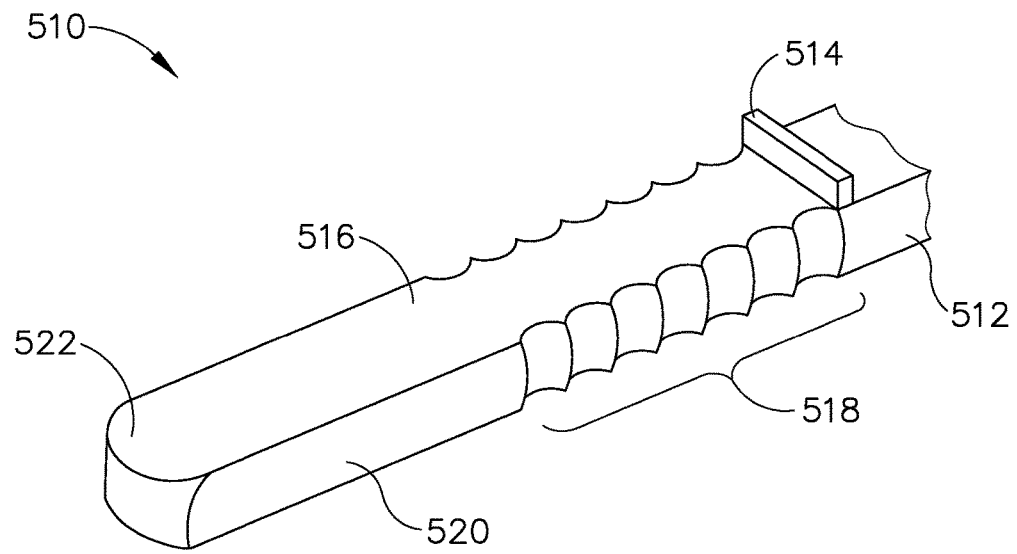
FIG. 23 depicts a perspective view of an exemplary threaded clamp arm that may be incorporated into the end effector of FIG. 3.
Figure 24:
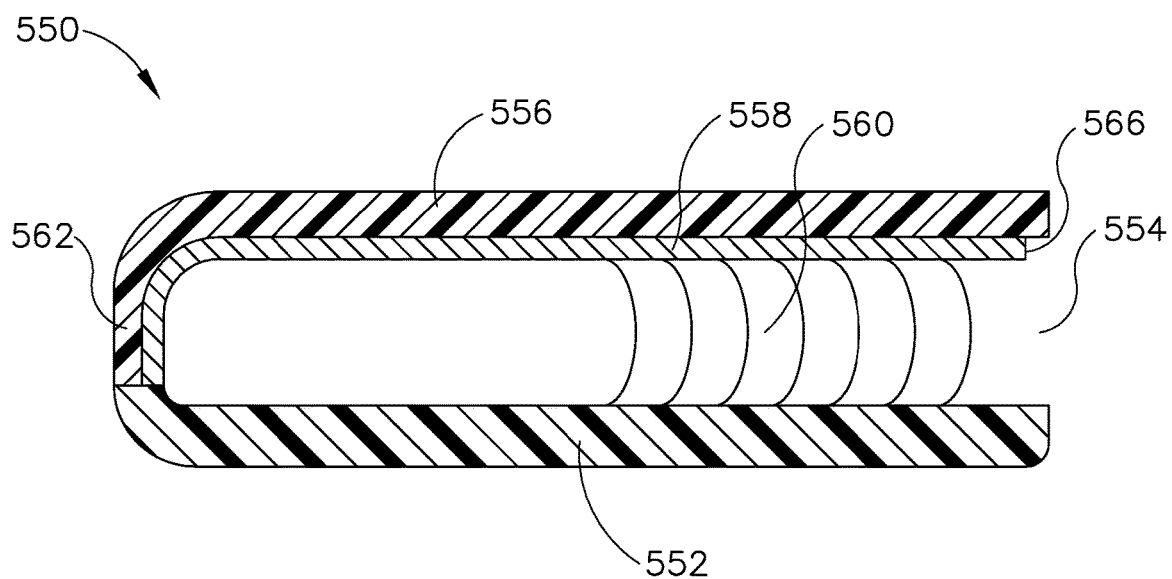
FIG. 24 depicts a cross-sectional side view of an exemplary threaded clamp pad configured to mate with the threaded clamp arm of FIG. 23.
Figure 25:
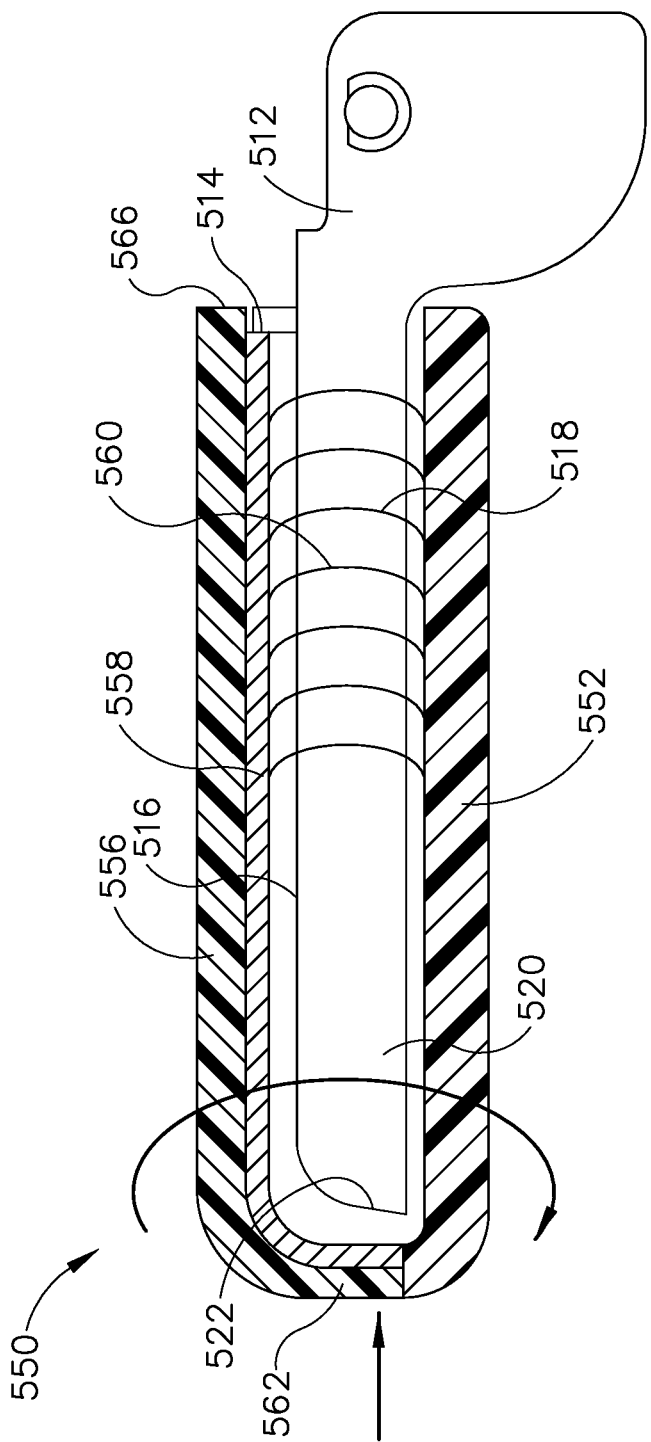
FIG. 25 depicts a cross-sectional side view of the threaded clamp pad of FIG. 24 secured to the threaded clamp arm of FIG. 23.
Figure 26A:
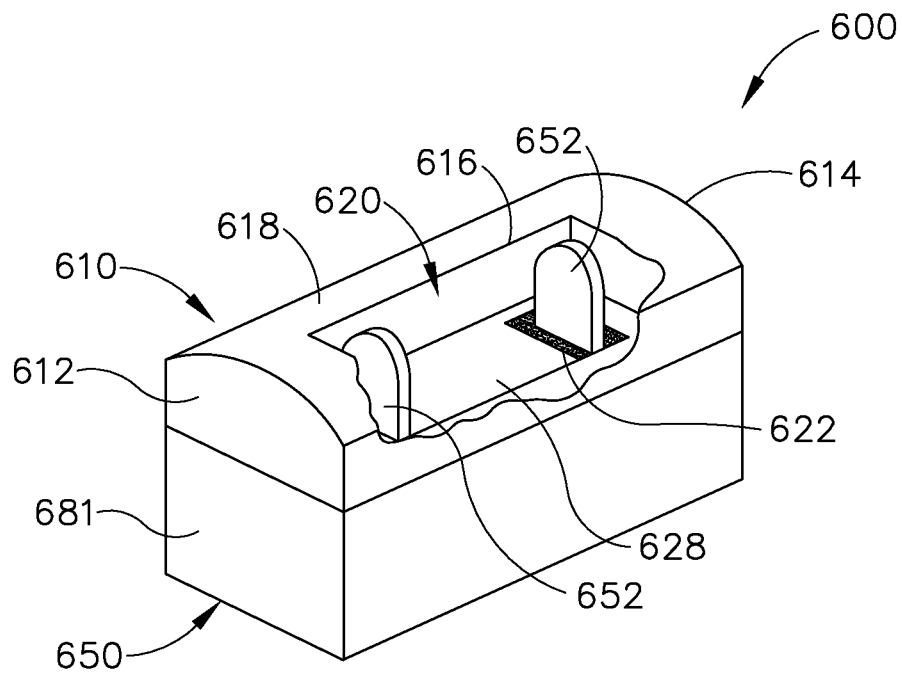
FIG. 26A shows a partial cutout perspective of an exemplary alternative clamp arm assembly that may be incorporated into the end effector of FIG. 3, with malleable tabs in a first configuration.
Figure 26B:
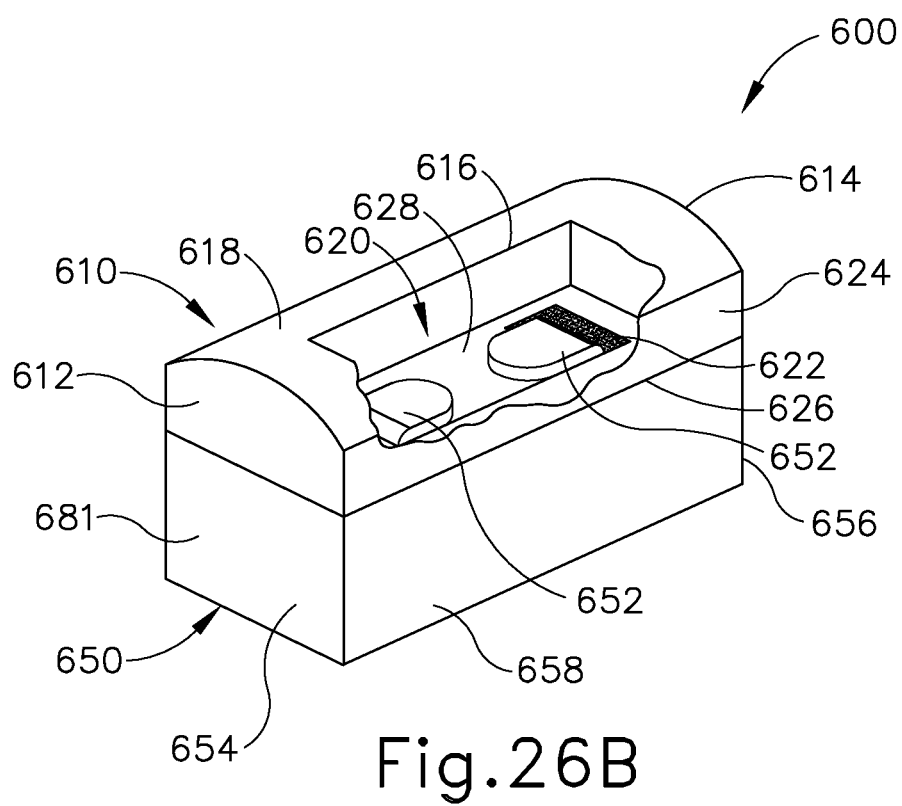
FIG. 26B shows a partial cutout perspective of the clamp arm assembly of FIG. 26A, with the malleable tabs in a second configuration.

FIGS. 23-25 show another exemplary clamp arm assembly (500) and related components that may be readily incorporated into end effector (50, 140) in place of clamp arm (56, 144) and clamp pad (58a, 58b, 146). Clamp arm assembly (500) of this example includes a threaded clamp arm (510) and a threaded clamp pad (550). Threaded clamp arm (510) includes a proximal end (512), a distal end (522), an external threaded region (518), a lead in nose (520) distal in relation to threaded region (518), an optional stop boss (514), and an elongate portion (516) connecting proximal end (512) to distal end (522).

Threaded clamp pad (550) includes a tissue contact pad (552), a proximal opening (554), a proximal end (566), a closed distal end (562), a casing (558) defining a complementary internal threaded region (560), and an optional polytetrafluoroethylene shell (556) surrounding casing (558).

As shown in FIG. 25, distal end (522) of threaded clamp arm (510) may be inserted into proximal opening (554) of threaded clamp pad (550). Lead in nose (520) of threaded clamp arm (510) may help reduce the chances of threaded region (518) and complementary threaded region (560) cross-threading. Once complementary threaded region (560) and threaded region (518) meet, an operator may rotate threaded clamp pad (550) around threaded clamp arm (510), thereby connecting threaded clamp arm (510) and threaded clamp pad (550). In the present example, threaded regions (518, 560) each comprise complementary helical threading to provide a screw-in relationship between clamp arm (510) and clamp pad (520). In some other versions, threaded regions (518, 560) each comprise complementary ribbing or teeth that provide a ratcheting slide-in relationship between clamp arm (510) and clamp pad (520).

Optional stop boss (514) may be positioned on threaded claiming arm (510) at a location where stop boss (514) will engage proximal end (566) of threaded clamp pad (550) at a position where tissue contact pad (552) is facing in the desired angular direction (i.e., with tissue contact pad (552) oriented to face blade (24, 79, 160)). Alternatively or additionally, optional polytetrafluoroethylene shell (556) surrounding casing (558) may be configured in such a way that closed distal end (562) engages distal end (522) of threaded clamp arm (510) at a location where stop boss (514) will engage proximal end (566) of threaded clamp pad (550) at a position where tissue contact pad (552) is facing in the desired angular direction (i.e., with tissue contact pad (552) oriented to face blade (24, 79, 160)).

As noted above, clamp pad (550) may be secured to clamp arm (510) simply by rotating clamp pad (550) about clamp arm (510) until clamp arm (510) grounds out against clamp pad (550). To remove clamp pad (550) for replacement, clamp pad (550) may simply be rotated in the opposite direction until threaded regions (518, 560) are disengaged from each other.

E. Replaceable Clamp Pads Having Fold Over Tabs

FIGS. 26A-33C show another exemplary clamp arm assembly (600) and related components that may be readily incorporated into end effector (50, 140) in place of clamp arm (56, 144) and clamp pad (58a, 58b, 146). Clamp arm assembly (600) of this example includes a clamp arm (610) and a clamp pad (650). As will be described in greater detail below, but initially shown in FIGS. 26A-26B, clamp arm (610) has a pair of tab slots (622) that are configured to receive foldable tabs (652) of clamp pad (650) in order to couple clamp arm (610) with clamp pad (650). It should be understood that FIGS. 26A-33C only show a portion of clamp arm assembly (600). In particular, the proximal end (614) of clamp arm (610) would include various features that would enable clamp arm (610) to pivotally mount to outer sheath (72, 132) and inner tube (76, 134) as described above. Such features may be configured and operable to receive pins (135, 145) just like clamp arm (144) described above. Alternatively, such features may be configured similar to coupling holes (52a, 52B) and studs (54b) of clamp arm (56) described above. Alternatively, clamp arm (610) may be mounted in any other suitable fashion.

As shown in FIGS. 26A-29, clamp arm (610) includes a proximal end (614), a distal end (612), a top (618), sides (624), and a bottom (626). Top (618) of clamp arm (610) partially defines a recess (620). Recess (620) is further defined by recess walls (616) and recess floor (628). Tab slots (622) extend from recess floor (628) to bottom (626) of clamp arm (610).

As shown in FIGS. 26A-26B and FIGS. 30-32, clamp pad (650) includes a body (651), a proximal end (656), a distal end (654), a bottom (664), a top (662), sides (658), and a set of foldable tabs (652) extending upwardly from a base (660). Base (660) may be unitarily coupled to foldable tabs (652). Base (660) and foldable tabs (652) may comprise of any suitable material, including but not limited to, aluminum, steel, malleable plastics, or any other suitable material known to a person having ordinary skill in the art in view of the teachings herein. Base (660) may be inserted within body (651), or fixedly secured to top (662). Base (660) may be fixedly secured to top (662) by any suitable methods, such as welding or any other suitable method known to a person having ordinary skill in the art in view of the teaching herein. Foldable tabs (652) are capable of folding toward top (662) of pad (650). Tabs (652) are malleable such that tabs (652) will maintain a bent configuration when tabs (652) are bent by the operator, as is shown in the sequence from FIG. 26A (un-bent configuration) to FIG. 26B (bent configuration).

Figure 33A:
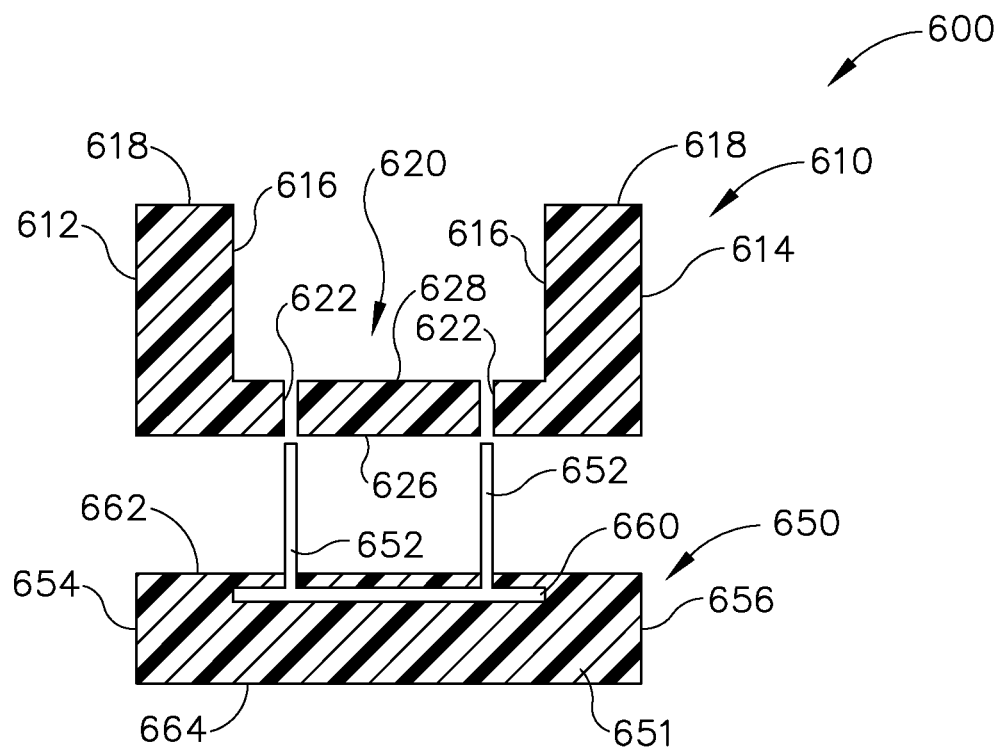
FIG. 33A depicts a cross-sectional view of the clamp pad of FIG. 30 separated from the clamp arm of FIG. 27.
Figure 33B:
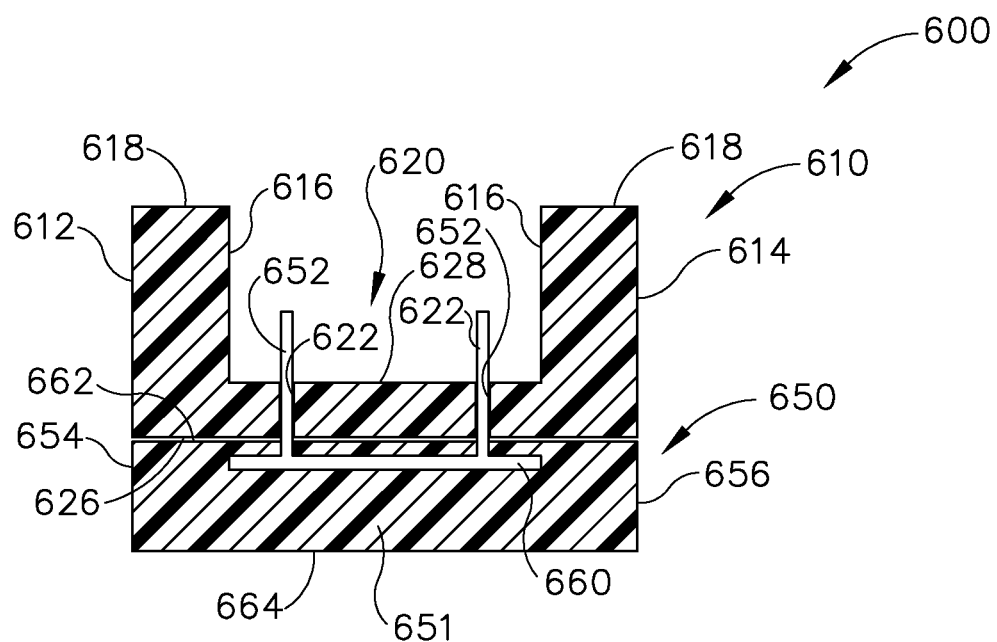
FIG. 33B depicts a cross-sectional view of the clamp pad of FIG. 30 engaged with the clamp arm of FIG. 27, with the malleable tabs in the first configuration.
Figure 33C:
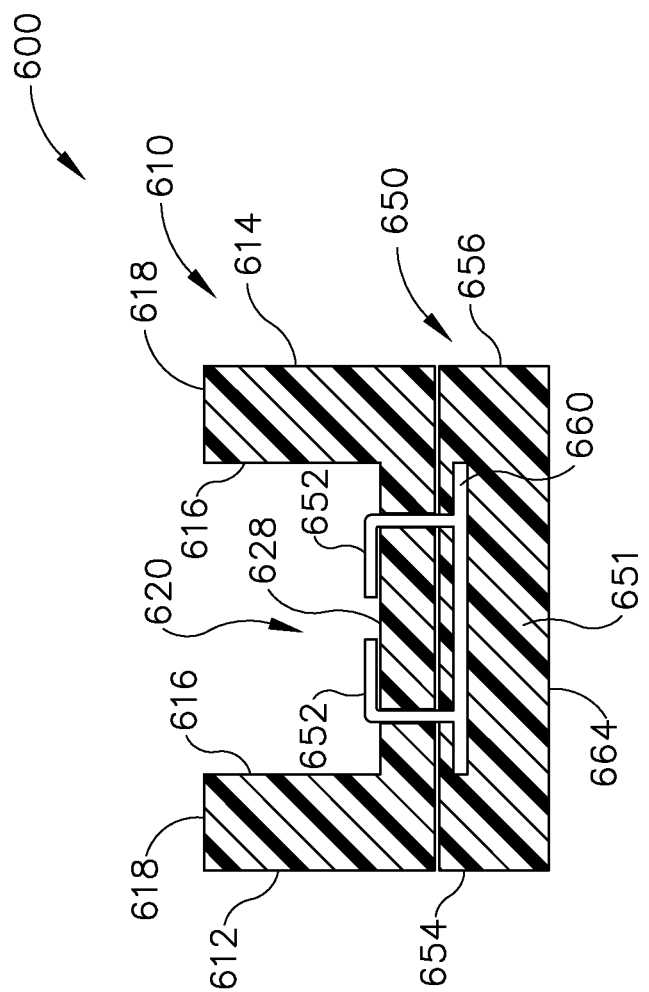
FIG. 33C depicts a cross-sectional view of the clamp pad of FIG. 30 engaged with the clamp arm of FIG. 27, with the malleable tabs in the second configuration.

FIGS. 33A-33C show how clamp pad (650) is attached to clamp arm (610). In FIG. 33A, clamp pad (650) is placed underneath clamp arm (610) in such a way that foldable tabs (652) are adjacent to tab slots (622) of clamp arm (610). Then, as shown in FIG. 33B, clamp pad (650) is inserted upwardly toward clamp arm (610) in such a way that foldable tabs (652) pass through tab slots (622), with a portion of foldable tabs (652) extending within recess (620) above tab slots (622). Additionally, bottom (626) of clamp arm (610) is in contact with top (662) of clamp pad (650). Optionally, distal end (612) of clamp arm (610) may align with distal end (654) of clamp pad (650) while proximal end (614) of clamp arm (610) may align with proximal end (656) of clamp pad. As shown in FIG. 33C, once foldable tabs (652) are inserted through tab slots (622), foldable tabs (652) may be folded toward recess bottom (628). While foldable tabs (652) are folded toward each other in FIG. 33C, it should be understood that tabs (652) may alternatively be folded away from each other—either toward sides (624, 658), toward ends (612, 614), or in any other suitable directions. As noted above, once tabs (652) are bent to the configuration shown in FIG. 33C, the malleable properties of tabs (652) will maintain this bent configuration of tabs (652), such that bent tabs (652) will effectively secure clamp pad (650) to clamp arm (610).

Recess (620) is dimensioned to allow an operator to access tabs (652) in such a way as to bend tabs (652) in a position to fix pad (650) to clamp arm (610), and to bend tabs (652) in a position to free pad (650) from clamp arm (610). Contact between tabs (652) and clamp arm (610) fixes the position of pad (650) relative to clamp arm (610) during a procedure while also allowing for pad (650) to be replaced when needed. In other words, if the operator wishes to replace clamp pad (650), the operator may bend tabs (652) back from the position shown in FIG. 33C to the position shown in FIG. 33B, which will allow the operator to pull a spent clamp pad (650) away from clamp arm (610) and thereby replace clamp pad (650) with a new clamp pad (650).

F. Replaceable Clamp Pad Inserted from Top of Clamp Arm

FIGS. 34-37 show another exemplary clamp arm assembly (700) and related components that may be readily incorporated into end effector (50, 140) in place of clamp arm (56, 144) and clamp pad (58a, 58b, 146). Clamp arm assembly (700) of this example includes a clamp arm (710), and a cartridge pad assembly (750). As will be described in greater detail below, cartridge pad assembly (750) is configured to be inserted from the top of clamp arm (710), while clamp arm (710) is configured to retain cartridge pad assembly (750) utilizing various retention methods.

Figure 34:
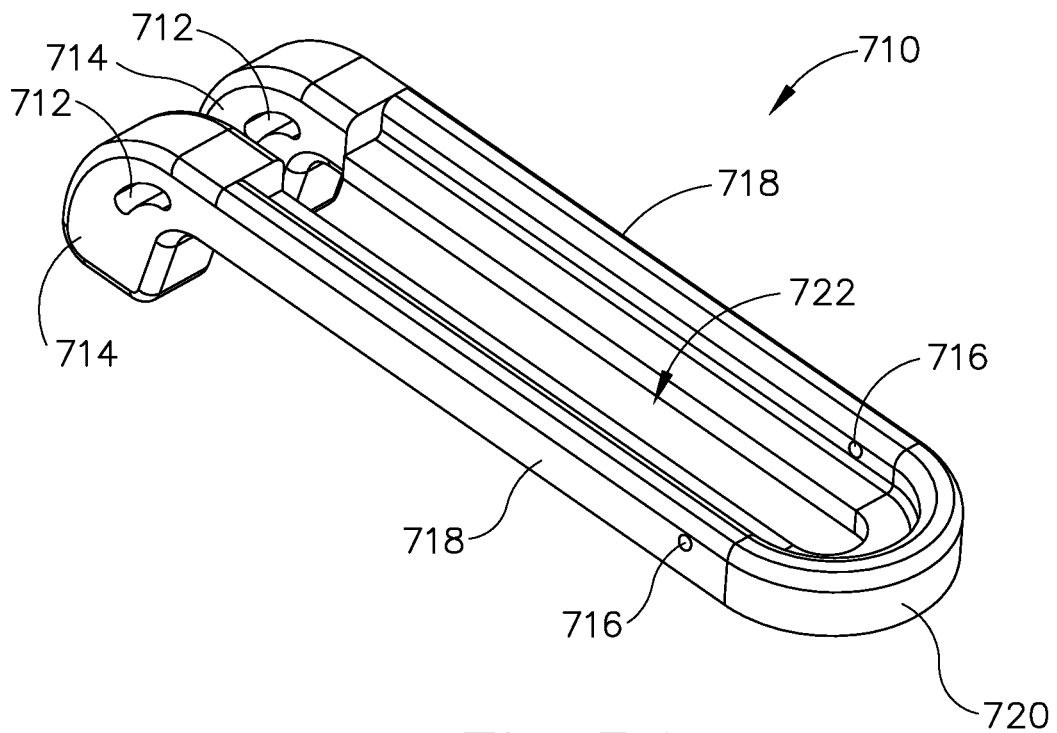
FIG. 34 depicts a perspective view of another exemplary clamp arm that may be incorporated into the end effector of FIG. 3.

FIG. 34 shows clamp arm (710) including a proximal end (714), a distal end (720), an elongated frame (718) extending from proximal end (714) to distal end (720), a pair of kidney slots (712), and a pair of laterally oriented distal openings (716). Elongated frame (718) further defines an opening (722) in which pad (756) may be inserted. Clamp arm (710) generally defines a "U" shape in this example.

Figure 35:
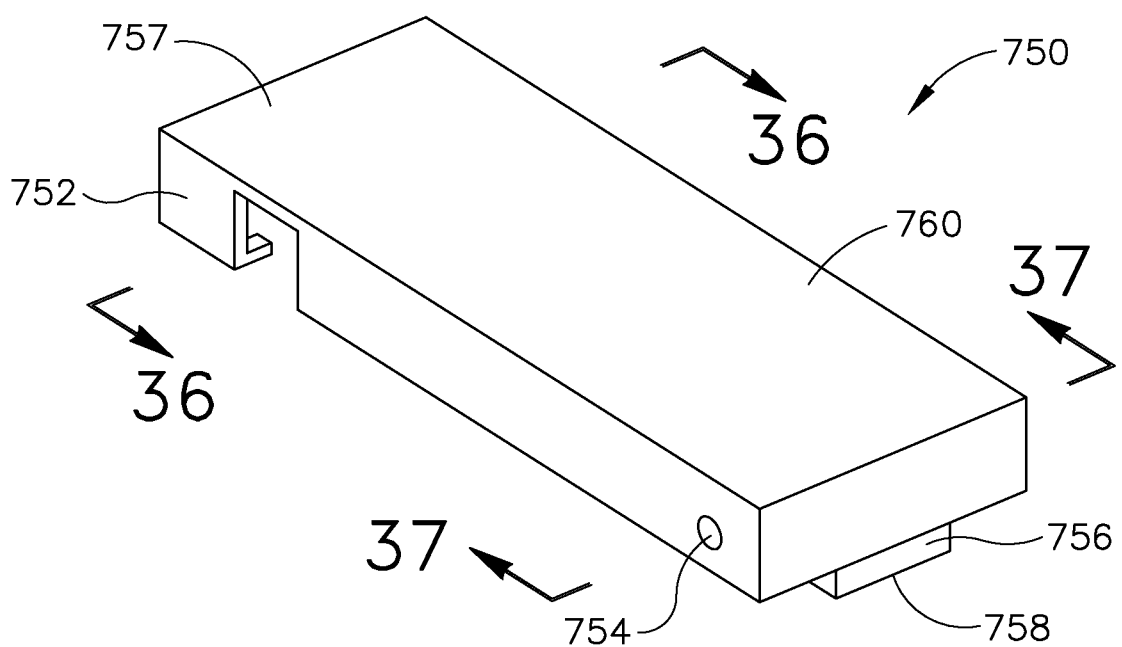
FIG. 35 depicts a perspective view of an exemplary clamp pad that may be coupled with the clamp arm of FIG. 34.

FIG. 35 show cartridge pad assembly (750) including a proximal end (757), a distal end (758), a clip-in cartridge (760) extending from proximal end (757) to distal end (758), a tissue contact pad (756) attached to the bottom of clip-in cartridge (760), a pair of legs (752) at proximal end (757), and a pair of laterally oriented distal openings (754) at distal end (758). Tissue contact pad (756) may be fixedly secured to clip-in cartridge (760) using any suitable features ore techniques as will be apparent to those of ordinary skill in the art in view of the teachings herein.

Figure 36:
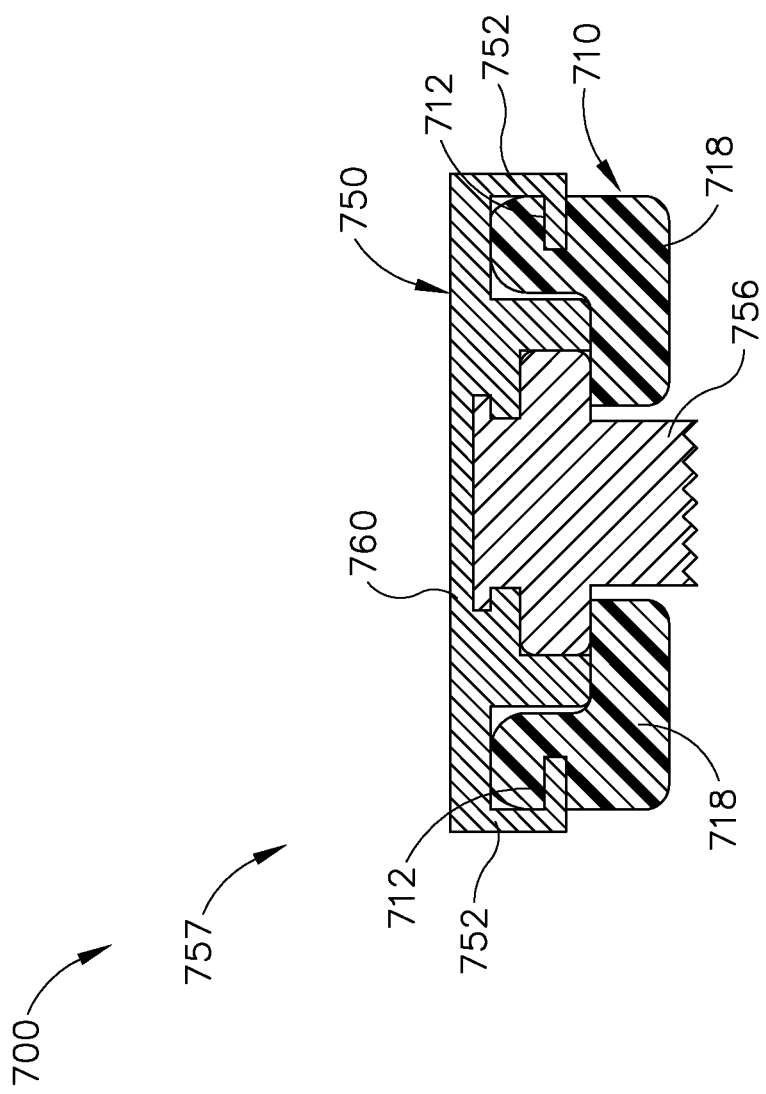
FIG. 36 depicts a cross-sectional view of the clamp pad of FIG. 35 coupled with the clamp arm of FIG. 34, taken along line 36-36 of FIG. 35.
Figure 37:
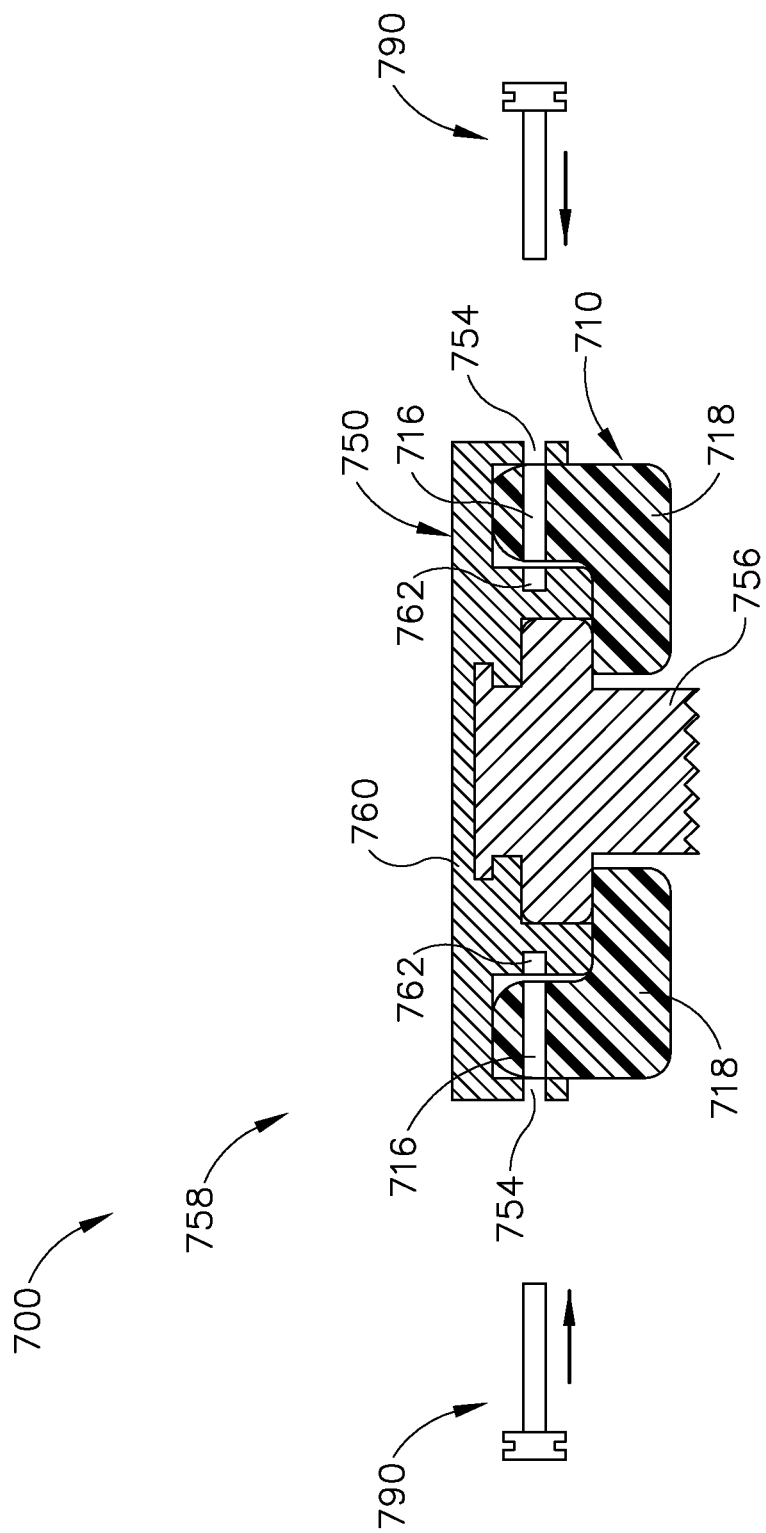
FIG. 37 depicts another cross-sectional view of the clamp pad of FIG. 35 coupled with the clamp arm of FIG. 34, taken along line 37-37 of FIG. 35.

FIGS. 36-37 show how cartridge pad assembly (750) is secured to clamp arm (710). In particular, FIG. 36 shows proximal end (757) where legs (752) of cartridge pad assembly (750) are inserted within kidney slots (712) of clamp arm (710). When legs (752) are first inserted into kidney slots (712), distal end (758) of cartridge pad assembly (750) forms an oblique angle with elongated frame (718). Once legs (752) travel along kidney slots (712), distal end (758) of cartridge pad assembly (750) becomes parallel with elongated frame (718) such that tissue contact pad (756) extends through elongated frame (718). Pad (756) also extends through elongated frame (718) in such a way that pad (756) may make contact with tissue without frame (718) also necessarily contacting tissue. Legs (752) and kidney slots (712) interact so that clip-in cartridge (760), and therefore pad (756), do not move relative to elongated frame (718) when distal end (758) of clip-in cartridge (750) is connected to elongated frame (718). It should be understood that legs (752) and kidney slots (712) cooperate to effectively secure the proximal end of cartridge pad assembly (750) to the proximal end of clamp arm (710).

FIG. 37 shows distal end (758) where openings (754) of cartridge pad assembly (750) are positioned to align with openings (716) of clamp arm (710). As can also be seen in FIG. 37, clip-in cartridge (760) includes recesses (762) that also align with openings (716, 754). It should be understood that openings (716, 754) and recesses (762) will be aligned when legs (752) reach the distal ends of respective kidney slots (712). With openings (716, 754) and recesses (762) aligned, a pair of pins (790) may be inserted into openings (716, 754) and recesses (762) to secure the distal end of cartridge pad assembly (750) to clamp arm (710).

While the foregoing example includes kidney slots (712) coupling with legs (752) and distal openings (716, 754) coupling with recesses (762) via pins (790), a variety of other structures and technique may be utilized to couple either or both proximal ends (714, 757) and distal ends (720, 758). For instance, clip-in cartridge (760) could be sized to provide an interference fit with the interior of elongated frame (718) in such a way that when clip-in cartridge is pressed against elongated frame (718), the interior of elongated frame (718) couples to clip-in cartridge (760). Other suitable methods of securing clip-in cartridge (760) to elongate frame (718) will be apparent to those of ordinary skill in the art in view of the teachings herein.

It should also be understood that the above described assembly method may be reversed to replace a spent cartridge pad assembly (750). In particular, the operator may simply remove pins (790) from openings (716, 754) and recesses (762), pivot distal end (758) of cartridge pad assembly (750) away from distal end (720) of clamp arm (710), and remove legs (752) from kidney slots (712) in order to decouple a spent cartridge pad assembly (750) from clamp arm (710). The operator may then perform the above-described assembly steps to secure a new cartridge pad assembly (750) to clamp arm (710). These assembly and disassembly steps may all be carried out without having to remove clamp arm (710) from the rest of instrument (20, 100).

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic instrument comprising: (a) a body; (b) a shaft assembly, wherein the shaft assembly extends distally from the body, wherein the shaft assembly comprises an acoustic waveguide, wherein the waveguide is configured to acoustically couple with an ultrasonic transducer; and (c) an end effector, wherein the end effector comprises: (i) an ultrasonic blade in acoustic communication with the waveguide, (ii) a clamp arm pivotally coupled with the shaft assembly, wherein the clamp arm further comprises a proximal portion and an elongated distal portion, and (iii) a clamp pad, wherein the clamp pad is configured to removably couple with the clamp arm while the clamp arm is pivotally coupled to the shaft assembly.

Example 2

The ultrasonic instrument of Example 1, wherein the elongated distal portion of the clamp arm further comprises: (i) an elongated flattened surface, and (ii) an elongated protrusion extending along the elongated flattened surface.

Example 3

The ultrasonic instrument of Example 2, wherein the clamp pad further comprises a sleeve configured to receive the elongated flattened surface and the elongated protrusion.

Example 4

The ultrasonic instrument of Example 3, wherein the clamp arm further comprises a pair of recesses, wherein the sleeve further comprises a pair of nubs configured to mate with the pair of recesses.

Example 5

The ultrasonic instrument of any one or more of Examples 1 through 4, wherein the elongated distal portion of the clamp arm further comprises a narrowed portion and an outwardly protruding head, wherein the narrowed portion is located proximally in relation to a protruding head.

Example 6

The ultrasonic instrument of any one or more of Examples 1 through 5, wherein the clamp pad further comprises an elastomeric tube, wherein the elastomeric tube is configured to slide over the protruding head.

Example 7

The ultrasonic instrument of any one or more of Examples 1 through 6, wherein the clamp arm further comprises a frame defining an opening, wherein the clamp pad further comprise a pad portion and a mating portion extending above the pad portion, wherein to mating portion is configured to extend through the opening.

Example 8

The ultrasonic instrument of Example 7, wherein the end effector further comprises a sliding lock, wherein the sliding lock is configured to engage the mating portion of the clamp pad.

Example 9

The ultrasonic instrument of any one or more of Examples 1 through 8, wherein the clamp arm further comprises a first threaded portion around the elongated distal portion, wherein the clamp pad further comprises a second threaded portion configured to mate with the first threaded portion.

Example 10

The ultrasonic instrument of any one or more of Examples 1 through 9, wherein the clamp arm further comprises a stop feature, wherein the stop feature is configured to engage a proximal end of clamp pad to orient the clamp pad relative to the clamp arm.

Example 11

The ultrasonic instrument of any one or more of Examples 1 through 10, wherein a distal end of the clamp pad is configured to selectively engage a distal end of the clamp arm to orient the clamp pad relative to the clamp arm.

Example 12

The ultrasonic instrument of any one or more of Examples 1 through 11, wherein the clamp pad further comprises a foldable tab.

Example 13

The ultrasonic instrument of Example 12, wherein the clamp arm further comprises a recess, wherein the recess comprises a floor, wherein the clamp arm further comprises a slot extending into the floor of the recess.

Example 14

The ultrasonic instrument of Example 13, wherein the foldable tab is configured to fold against the floor of the recess.

Example 15

The ultrasonic instrument of any one or more of Examples 1 through 14, wherein the clamp pad further comprises a padded portion and a cartridge, wherein the cartridge is fixed to the padded portion.

Example 16

The ultrasonic instrument of Example 15, wherein the clamp arm comprises an elongated frame defining a slot, wherein the padded portion is configured to enter the slot, wherein the cartridge is configured to couple with the elongated frame.

Example 17

The ultrasonic instrument of Example 16, wherein the elongated frame comprises a kidney slot, wherein the cartridge further comprises a leg configured to mate with the kidney slot.

Example 18

The ultrasonic instrument of any one or more of Examples 1 through 17, wherein the elongated frame comprises first, hole wherein the cartridge further comprises a second hole, wherein the end effector further comprises a pin, wherein the pin is configured to fit in the first hole and the second hole to thereby secure at least a portion of the clamp pad to the clamp arm.

Example 19

An ultrasonic instrument comprising: (a) a body; (b) a shaft assembly, wherein the shaft assembly comprises an acoustic waveguide, wherein the waveguide is configured to acoustically couple with an ultrasonic transducer; and (c) an end effector; wherein the end effector comprises: (i) an ultrasonic blade in acoustic communication with the waveguide, (ii) a clamp arm pivotally coupled with the shaft assembly, and (iii) a clamp pad, wherein the clamp pad and the clamp arm are configured to enable the clamp pad to be secured to the clamp arm while the clamp arm is pivotally coupled to the shaft assembly, wherein the clamp pad and the clamp arm are further configured to enable the clamp pad to be removed from the clamp arm while the clamp arm is pivotally coupled to the shaft assembly.

Example 20

An instrument for installing a clamp pad on a clamp arm and and removing a clamp pad from a clamp arm, wherein the instrument comprises: (a) a body comprising a first end and second end; (b) a pad installation portion associated with the first end, wherein the pad installation portion comprises an installation channel configured to house the clamp pad; and (c) a pad removal portion associated with the second end, wherein the pad removal portion comprises: (i) a removal channel configured to receive a clamp pad installed on a clamp arm, and (ii) a pad removal feature located within the removal tube, wherein the pad removal feature is configured to selectively disengage at least a portion of the clamp pad from the clamp arm.

VI. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic instrument comprising:
   (a) a shaft assembly, wherein the shaft assembly comprises an acoustic waveguide, wherein the waveguide is configured to acoustically couple with an ultrasonic transducer; and
   (b) an end effector, wherein the end effector comprises:
      (i) an ultrasonic blade in acoustic communication with the waveguide,
      (ii) a clamp arm pivotally coupled with the shaft assembly, wherein the clamp arm further comprises a proximal portion and an elongated distal portion defining a recess, and
      (iii) a clamp pad defining an interior sleeve comprising a T-shaped configuration, wherein the T-shaped configuration of the interior sleeve of the clamp pad is configured to house the elongated distal portion and the recess in a single predefined orientation in order to removably couple the clamp pad with the clamp arm while the clamp arm is pivotally coupled to the shaft assembly.

2. The ultrasonic instrument of claim 1, wherein the elongated distal portion of the clamp arm further comprises:
   (i) an elongated flattened surface, and
   (ii) an elongated protrusion extending along the elongated flattened surface.

3. The ultrasonic instrument of claim 2, wherein the interior sleeve is configured to house both the elongated flattened surface and the elongated protrusion.

4. The ultrasonic instrument of claim 3, wherein the pad relative to the clamp arm.

5. An ultrasonic instrument comprising:
   (a) a shaft assembly, wherein the shaft assembly comprises an acoustic waveguide, wherein the waveguide is configured to acoustically couple with an ultrasonic transducer; and
   (b) an end effector; wherein the end effector comprises:
      (i) an ultrasonic blade in acoustic communication with the waveguide,
      (ii) a clamp arm pivotally coupled with the shaft assembly, wherein the clamp arm comprises an elongated distal portion having a T-shaped external perimeter, and
      (iii) a clamp pad defining a complimentary T-shaped interior sleeve,
      wherein the clamp pad and the clamp arm are configured to enable the clamp pad to be secured to the clamp arm while the clamp arm is pivotally coupled to the shaft assembly, wherein the complementary T-shaped interior sleeve of the clamp pad is configured to encompass a cross-sectional surface of the T-shaped external perimeter of the elongated distal portion when the clamp pad is secured to the clamp arm to thereby align the clamp pad relative to the clamp arm in a predefined orientation,
      wherein the clamp pad and the clamp arm are further configured to enable the clamp pad to be removed from the clamp arm while the clamp arm is pivotally coupled to the shaft assembly.

6. An ultrasonic instrument comprising:
   (a) a shaft assembly, wherein the shaft assembly comprises an acoustic waveguide, wherein the waveguide is configured to acoustically couple with an ultrasonic transducer; and
   (b) an end effector, wherein the end effector comprises:
      (i) an ultrasonic blade in acoustic communication with the waveguide,
      (ii) a clamp arm pivotally coupled with the shaft assembly, wherein the clamp arm further comprises a proximal portion and an elongated distal portion, wherein the elongated distal portion defines a coupling recess, wherein the elongated distal portion comprises a flattened surface and a corresponding elongated rib, wherein the flattened surface and the corresponding elongated rib together form a T-shaped configuration and (iii) a clamp pad comprising a coupling protrusion, wherein the clamp pad defines an interior sleeve comprising a corresponding T-shaped configuration, wherein the coupling protrusion is housed within the interior sleeve, wherein the interior sleeve of the clamp pad is configured receive the elongated distal portion of the clamp arm such that the coupling recess houses the coupling protrusion in order to removably couple the clamp pad with the clamp arm while the clamp arm is pivotally coupled to the shaft assembly, wherein the T-shaped configuration of the elongated distal portion is dimensioned to be received within the corresponding T-shaped configuration of the interior sleeve in a singular pre-defined orientation.

* * * * *